US 7,329,518 B2

(12) United States Patent
Kawano et al.

(10) Patent No.: US 7,329,518 B2
(45) Date of Patent: Feb. 12, 2008

(54) ENZYME FOR PRODUCING OPTICALLY ACTIVE PYRIDINEETHANOL DERIVATIVES

(75) Inventors: Shigeru Kawano, Suita (JP); Miho Horikawa, Takasago (JP); Yoshihiko Yasohara, Himeji (JP); Junzo Hasegawa, Akashi (JP)

(73) Assignee: Kaneka Corporation, Osaka (JP)

( * ) Notice: Subject to any disclaimer, the term of this patent is extended or adjusted under 35 U.S.C. 154(b) by 383 days.

(21) Appl. No.: 10/669,503

(22) Filed: Sep. 25, 2003

(65) Prior Publication Data

US 2004/0043460 A1 Mar. 4, 2004

Related U.S. Application Data

(62) Division of application No. 09/787,746, filed as application No. PCT/JP00/04237 on Jun. 28, 2000, now abandoned.

(30) Foreign Application Priority Data

Jul. 21, 1999 (JP) ............................... 11-206503

(51) Int. Cl.
C12N 9/04 (2006.01)
C12N 15/00 (2006.01)
C12Q 1/32 (2006.01)
C12P 21/04 (2006.01)
C07H 21/04 (2006.01)

(52) U.S. Cl. .................... 435/190; 435/69.1; 435/71.1; 435/440; 435/26; 536/23.2; 536/23.7

(58) Field of Classification Search ............... 435/189, 435/4, 6, 25, 18, 69.1, 71.1, 440, 190, 26; 536/23.2, 23.7
See application file for complete search history.

(56) References Cited

U.S. PATENT DOCUMENTS 5,385,833 A 1/1995 Bradshaw et al.

(Continued)

FOREIGN PATENT DOCUMENTS

JP 61-227791 A 10/1986

(Continued)

OTHER PUBLICATIONS

Zmljewskl et al., "Enantioselective reduction of 3,4-methylene-diosyphenylacetone using *Candida famata* and *Zygosaccharomyces rouxii*" (1997) *Appl. Microbiol Biotechnol.* 47, pp. 162-166 (XP001205741).

(Continued)

*Primary Examiner*—Yong D. Pak
(74) *Attorney, Agent, or Firm*—Connolly Bove Lodge and Hutz

(57) ABSTRACT

The present invention relates to a method of producing an optically active pyridineethanol derivative. More particularly, it relates to a method of producing an optically active polycyclic pyridineethanol derivative by causing an enzyme or enzyme source to act on polycyclic acetylpyridine derivatives.

The present invention also relates to a novel enzyme which can be used in the production method mentioned above, a DNA coding for said enzyme, a recombinant vector having said DNA, and a transformant having said recombinant vector.

The invention further relates to a method of producing an optically active polycyclic pyridineethanol derivative by causing the above novel enzyme or the above transformant to act on optically inactive polycyclic pyridineethanol derivatives.

1 Claim, 2 Drawing Sheets

U.S. PATENT DOCUMENTS 6,037,158 A    3/2000   Hummel et al.

FOREIGN PATENT DOCUMENTS

| JP | 1-211494 A | 8/1989 |
| JP | 4-164069 A | 6/1992 |
| JP | 11-290092 A | 10/1999 |
| PL | 177372 B1 | 11/1999 |

OTHER PUBLICATIONS

Mitsuhiro Takeshita et al, Heterocycles. Synthesis of optically active hetero alkylaryl alcohols by baker's yeast (1987) vol. 26, No. 12, pp. 3051-3054.

David Bailey et al, Tetrahedron: Asymmetry. Preparation of highly enantiopure pyridylethanols by baker's yeast reductions (1993) vol. 4, No. 6, pp. 1255-1258.

Curt Bradshaw et al, J. Org. Chem. *Lactobacillus kafir* Alcohol dehydrogenase: A useful catalyst for synthesis (Feb. 28, 1992) vol. 57, No. 5, pp. 1532-1536.

Yoshinobu Naoshima et al, Recent Res. Devel. in Phytochem., 2. Biotransformations by plant cell cultures: Preparation of chiral alcohols by enantioselective reduction of organic compounds with Immobilized cells of carrot (1998) pp. 11-21.

P. N. Patil et al, Biotechnology Letters. Enantiomeric synthesis of pyridyl-1-ethanols using *rhizopus arrhizus* (Feb. 1996) vol. 18, No. 2, pp. 159-162.

Robert Seemayer et al, Tetrahedron: Asymmetry. Preparation of optically pure pyridyl-1-ethanols (1992) vol. 3, No. 7, pp. 827-830.

Dogdan Jarosz et al., "Enantiospecific reduction of prochiralketons aromatic type to optically active alcohols in *Nigrospora oryzae* culture", J. Basic Microbiol. (1996), vol. 36, No. 4, pp. 245-253.

Hummel, "Reduction of acetophenone to R(+)-phenylethanol by a new alcohol dehydrogenase from *Lactobacillus kefir*.", Appl. Microbiol. Biotechnol (1990) 34:15-19.

SEQ. ID. NO. 1

Fig. 1

```
          10        20        30        40        50        60        70        80        90
CAGCTGACGAGATGCTGTTTAGTGCCAACTATAAATACAGCTGGCTTTTGCCAAGGACAATTGCAACCGATTTCTATGGCATCAGGACTT 100       110       120       130       140       150       160       170       180
TCAAGATTGCAGCACAAGCTCCTCATCTAGTTCAAAAATCACACAGCTCAACATGTCCTACAATTTTGCCAACAAAGTTCTTATTGTGAC
                                                    M  S  Y  N  F  A  N  K  V  L  I  V  T 190       200       210       220       230       240       250       260       270
CGGAGGTCTGTCCGGTATTGGACTTGCAGTTGCAAAGAAGTTTCTTCAACTCGGGGCCAAAGTGACAATTTCTGATATTTCTGCCACTGA
 G  G  L  S  G  I  G  L  A  V  A  K  K  F  L  Q  L  G  A  K  V  T  I  S  D  I  S  A  T  E 280       290       300       310       320       330       340       350       360
AAAGTACAACACCGTTGTAGGTGAGTTCAAAACCGAGGGCATTGATGTCAAGAATGTTCAGTATATTCAGGCCGATGCAAGCAAAGAGGC
  K  Y  N  T  V  V  G  E  F  K  T  E  G  I  D  V  K  N  V  Q  Y  I  Q  A  D  A  S  K  E  A 370       380       390       400       410       420       430       440       450
CGACAACGAGAAGCTCATCTCCGAGACACTGTCTGCTTTCGGTGATCTCGACTACGTGTGCGCAAATGCTGGAATTGCCACTTTCACACA
  D  N  E  K  L  I  S  E  T  L  S  A  F  G  D  L  D  Y  V  C  A  N  A  G  I  A  T  F  T  Q 460       470       480       490       500       510       520       530       540
GACTACAGATATCTCCTACGACGTCTGGAGGAAGGTAACCAGCATTAATCTTGACGGTGTTTTCATGCTTGATAAACTAGCTGCACAATA
  T  T  D  I  S  Y  D  V  W  R  K  V  T  S  I  N  L  D  G  V  F  M  L  D  K  L  A  A  Q  Y 550       560       570       580       590       600       610       620       630
CTTTTTGAGCAAGAACAAGCCCAGCTGCTATTGTCAACATGGGTTCCATTCACTCGTATGTGGCCGCTCCTGGACTTTCTCACTACGGTGC
  F  L  S  K  N  K  P  G  A  I  V  N  M  G  S  I  H  S  Y  V  A  A  P  G  L  S  H  Y  G  A 640       650       660       670       680       690       700       710       720
GGCCAAAGGAGGTCTGAAGCTACTGACTCAGACCATGGCCCTTGAGTATGCCGCAAAAGGTATAAGAGTTAACTCGGTCAATCCTGGTTA
  A  K  G  G  L  K  L  L  T  Q  T  M  A  L  E  Y  A  A  K  G  I  R  V  N  S  V  N  P  G  Y 730       740       750       760       770       780       790       800       810
CATCAAGACACCATTGCTTGATATTTGCCCTAAAGAACACATGGATTACCTTATCACTCAGCATCCAATTGGACGTCTCGGAAAGCCTGA
  I  K  T  P  L  L  D  I  C  P  K  E  H  M  D  Y  L  I  T  Q  H  P  I  G  R  L  G  K  P  E 820       830       840       850       860       870       880       890       900
AGAGATTGCAAGTGCTGTTGCATTTCTGTGCTCTGACGAGGCTACATTTATCAACGGAATCTCCTTGTTGGTAGACGGTGGTTATACCGC
  E  I  A  S  A  V  A  F  L  C  S  D  E  A  T  F  I  N  G  I  S  L  L  V  D  G  G  Y  T  A 910       920       930       940       950       960       970       980
AAGATAATTGGAGGGCTACGAAGTTATGGTTTATGCTTCTGTATTGTCTTTCTTAAAAAGTCTTGACGGGTGCAC
  R
```

ENZYME FOR PRODUCING OPTICALLY ACTIVE PYRIDINEETHANOL DERIVATIVES

This application is a divisional of U.S. patent application Ser. no. 09/787,746, filed Jun. 28, 2000, which is the national stage of PCT/JP00/04237.

TECHNICAL FIELD

The present invention relates to a method of producing an optically active pyridineethanol derivative. More particularly, it relates to a method of producing an optically active polycyclic pyridineethanol derivative by causing an enzyme or enzyme source to act on polycyclic acetylpyridine derivatives.

The present invention also relates to a novel enzyme which can be used in the production method mentioned above, a DNA coding for said enzyme, a recombinant vector having said DNA, and a transformant having said recombinant DNA.

The invention further relates to a method of producing an optically active polycyclic pyridineethanol derivative by causing the above novel enzyme or the above transformant to act on an optically inactive polycyclic pyridineethanol derivative.

BACKGROUND ART

Optically active pyridineethanol derivatives are compounds useful as starting materials and intermediates of the synthesis of medicinals, agrochemicals and the like, which are required to be optically active.

As for the production of an optically active monocyclic pyridineethanol derivative, a method is known which comprises converting an acetylpyridine to the simplest optically active pyridineethanol derivative, namely hydroxyethylpyridine, using baker's yeast or like microorganisms (Japanese Kokai Publication Sho-61-22791), for instance.

As for the production of an optically active polycyclic pyridineethanol derivative, some methods are known: the method comprising effecting optical resolution of racemic 5-(1-hydroxyethyl)furo[2,3-c]pyridine or 5-(1-hydroxyethyl)-3-methylfuro[2,3-c]pyridine through asymmetric esterification using lipase type 2 from swine pancreatic (WO 9635678), and the method comprising effecting optical resolution of racemic 7-chloro-5-(1-hydroxyethyl)furo[2,3-c]pyridine through asymmetric esterification using *Candida antarctica* lipase (Synlett, 41, (1999)), for instance. However, these methods are based on optical resolution, hence the yield of one enantiomer is at most 50%, which is low and unsatisfactory.

Further, a method is known which comprises chemically reducing 5-(1-acetyl)-7-chloro-3-methylfuro[2,3-c]pyridine with (−)-chlorodiisopinocampheylborane in tetrahydrofuran to thereby obtain (S)-7-chloro-5-(1-hydroxyethyl)-3-methylfuro[2,3-c]pyridine (Journal of Organic Chemistry, 63, 7851 (1998)). Since, however, the expensive reducing agent is used in large amounts, it is difficult to put the method into practical use.

DISCLOSURE OF THE INVENTION

As a result of intensive investigations made by the present inventors to develop an efficient method of producing an optically active polycyclic pyridineethanol derivative, they discovered an enzyme source which has not been reported as yet but which is capable of stereoselectively reducing an acetylpyridine derivative and thus converting it to an optically active pyridineethanol derivative and this finding has now led to completion of the present invention.

Thus, the present invention is concerned with a method of producing an optically active pyridineethanol derivative represented by the general formula [2]:

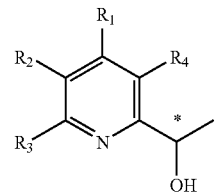

[2]

wherein $R_1$ and $R_2$ are bound to each other to form a 5- to 8-membered monocyclic heterocycle containing at least one hetero atom selected from the group consisting of oxygen, sulfur and nitrogen atoms, which heterocycle may optionally have a substituent(s), or a polycyclic heterocycle resulting from the condensation of such monocyclic heterocycle with another ring, which polycyclic heterocycle may optionally have a substituent(s), $R_3$ and $R_4$ are the same or different and each represents a hydrogen atom, a halogen atom, a hydroxyl group, an alkyl group containing 1 to 12 carbon atoms, which may optionally have a substituent(s), or an alkoxy group containing 1 to 12 carbon atoms, which may optionally have a substituent(s), and * indicates that the asterisked carbon atom is an asymmetric one, which method comprises stereoselectively reducing an acetylpyridine derivative represented by the general formula [1]:

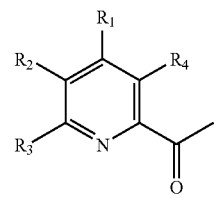

[1]

wherein $R_1$, $R_2$, $R_3$ and $R_4$ are as defined above, by causing an enzyme or enzyme source capable of asymmetrically reducing the same to act thereon.

In a preferred mode of embodiment, the invention relates to a method of producing an optically active pyridineethanol derivative represented by the general formula [4]:

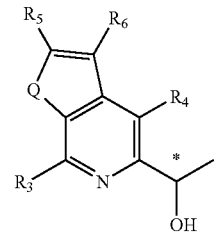

[4]

wherein Q represents an oxygen or sulfur atom or a group of the general formula -N(D)-, in which N is a nitrogen atom and D represents a hydrogen atom or a monovalent protective group, $R_3$, $R_4$, $R_5$ and $R_6$ are the same or different and each represents a hydrogen atom, a halogen atom, a hydroxyl group, an alkyl group containing 1 to 12 carbon atoms, which may optionally have a substituent(s), or an alkoxy group containing 1 to 12 carbon atoms, which may optionally have a substituent(s), and * indicates that the asterisked carbon atom is an asymmetric one, which method comprises stereoselectively reducing an acetylpyridine derivative represented by the general formula [3]:

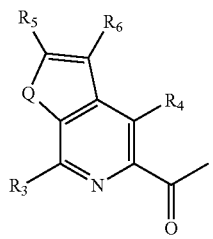

[3]

wherein Q, $R^3$, $R^4$, $R^5$ and $R^6$ are as defined above, by causing an enzyme or enzyme source capable of asymmetrically reducing the same to act thereon.

The invention further relates to an enzyme having the following physical and chemical properties (1) to (3):

(1) Activity: It stereoselectively reduces 5-acetylfuro[2,3-c]pyridine, in the presence of reduced form nicotinamide adenine dinucleotide as a coenzyme, to give 5-(1-(R)-hydroxyethyl)furo[2,3-c]pyridine;

(2) Specificity: It has reducing ability against ketones and aldehydes but is very low in reducing activity against carbocyclic ketones and the α-position keto group of α-keto acids;

(3) Molecular weight: It shows a molecular weight of about 60,000 in gel filtration analysis and a molecular weight of about 29,000 in SDS polyacrylamide electrophoresis.

The invention also relates to an enzyme specified below under (a) or (b):

(a) An enzyme comprising an amino acid sequence shown under SEQ ID NO:1 in the sequence listing;

(b) An enzyme comprising an amino acid sequence derived from the amino acid sequence shown under SEQ ID NO:1 in the sequence listing by deletion, substitution and/or addition of one or several amino acids and having an activity by which 5-acetylfuro[2,3-c]pyridine is stereoselectively reduced to 5-(1-(R)-hydroxyethyl)furo[2,3-c]pyridine.

When these enzymes are used as the enzyme in the production method mentioned above, an optically active pyridineethanol derivative having the R absolute configuration is obtained.

Furthermore, the invention relates to a DNA coding for such enzyme or a DNA comprising a base sequence shown under SEQ ID NO:2 in the sequence listing. It further relates to a recombinant vector containing such DNA and to a transformant having such recombinant vector.

When this transformant is used as a source of said enzyme in the above production method, an optically active pyridineethanol derivative having the R absolute configuration is obtained.

Still further, the invention relates to a method of producing an optically active pyridineethanol derivative having the S absolute configuration and represented by the general formula [6]:

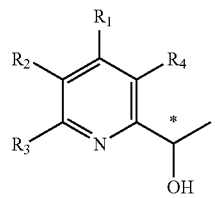

[6]

wherein $R_1$ and $R_2$ are bound to each other to form a 5- to 8-membered monocyclic heterocycle containing at least one hetero atom selected from the group consisting of oxygen, sulfur and nitrogen atoms, which heterocycle may optionally have a substituent(s), or a polycyclic heterocycle resulting from the condensation of such monocyclic heterocycle with another ring, which polycyclic heterocycle may optionally have a substituent(s), $R_3$ and $R_4$ are the same or different and each represents a hydrogen atom, a halogen atom, a hydroxyl group, an alkyl group containing 1 to 12 carbon atoms, which may optionally have a substituent(s), or an alkoxy group containing 1 to 12 carbon atoms, which may optionally have a substituent(s), and * indicates that the asterisked carbon atom is an asymmetric one, which method comprises causing the enzyme and/or transformant mentioned above to act on a pyridineethanol derivative represented by the general formula [5]:

[5]

wherein $R_1$, $R_2$, $R_3$ and $R_4$ are as defined above, to thereby preferentially oxidize the R form of the pyridineethanol derivative and recovering the remaining S form of the pyridineethanol derivative.

In a preferred mode of embodiment, the invention relates to a method of producing an optically active pyridineethanol derivative having the S absolute configuration and represented by the general formula [8]:

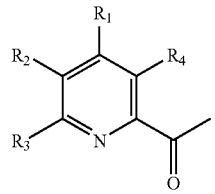

[1]

In the above general formula [1], $R_1$ and $R_2$ are bound to each other to form a 5- to 8-membered monocyclic heterocycle containing at least one hetero atom selected from the group consisting of oxygen, sulfur and nitrogen atoms, which heterocycle may optionally have a substituent(s), or a polycyclic heterocycle resulting from the condensation of such monocyclic heterocycle with another ring, which polycyclic heterocycle may optionally have a substituent(s).

Specifically, the 5-membered monocyclic heterocycle includes, among others, the furan, dihydrofuran, pyrrole, pyrroline, dehydrodioxolane, pyrazole, pyrazoline, imidazole, oxazole, isoxazole, oxadiazole, triazole, thiazole, thiophene, dihydrothiophene and like rings. The 6-membered monocyclic heterocycle includes, among others, the pyran, dihydropyran, pyridine, dihydropyridine, tetrahydropyridine, dehydrodioxane, dehydromorpholine, pyridazine, dihydropyridazine, pyrimidine, dihydropyrimidine, tetrahydropyrimidine, pyrazine, dihydropyrazine and like rings. The 7-membered monocyclic heterocycle includes, among others, the cycloheptane, cycloheptadiene and cycloheptatriene rings each substituted by a nitrogen, oxygen or sulfur atom or atoms, and the thiazepine and like rings. The 8-membered monocyclic heterocycle includes, among others, the cyclooctene, cyclooctadiene and cyclooctatetraene rings each substituted by a nitrogen, oxygen or sulfur atom or atoms and the like rings. The polycyclic heterocycle includes, among others, the benzofuran, isobenzofuran, chromene, indolidine, indole, isoindole, isoquinoline, phthalazine, naphthyridine, quinoxaline and benzothiophene rings, hydrogenated versions of these rings, and so forth.

These heterocycles may each have a substituent(s). As such substituent, there may be mentioned, for example, a halogen atom, a hydroxyl group, an alkyl group containing 1 to 12 carbon atoms and an alkoxy group containing 1 to 12 carbon atom.

Among the heterocycles specifically mentioned above, 5-membered monocyclic heterocycles are preferred. The furan ring, either substituted or unsubstituted, is more preferred and the furan ring is most preferred.

In the above general formula [1], $R_3$ and $R_4$ are the same or different and each represents a hydrogen atom, a halogen atom, a hydroxyl group, an alkyl group containing 1 to 12 carbon atoms, which may optionally have a substituent(s), or an alkoxy group containing 1 to 12 carbon atoms, which may optionally have a substituent(s). Specifically, there may be mentioned a hydrogen atom, chlorine atom, bromine atom, fluorine atom, hydroxyl group, methyl group, ethyl group, methoxy group and ethoxy group, etc. As the substituent(s) which the above alkyl and alkoxy groups may have, there may be mentioned a hydroxyl group, a halogen

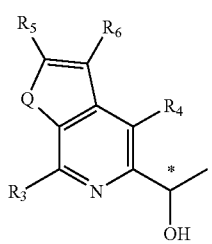

[8]

wherein Q represents an oxygen or sulfur atom or a group of the general formula -N(D)-, in which N is a nitrogen atom and D represents a hydrogen atom or a monovalent protective group, $R_3$, $R_4$, $R_5$ and $R_6$ are the same or different and each represents a hydrogen atom, a halogen atom, a hydroxyl group, an alkyl group containing 1 to 12 carbon atoms, which may optionally have a substituent(s), or an alkoxy group containing 1 to 12 carbon atoms, which may optionally have a substituent(s), and * indicates that the asterisked carbon atom is an asymmetric one, which method comprises causing the enzyme and/or transformant mentioned above to act on a pyridineethanol derivative represented by the general formula [7]:

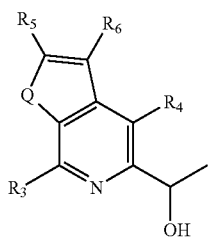

[7]

wherein Q, $R_3$, $R_4$, $R_5$ and $R_6$ are as defined above, to thereby preferentially oxidize the R form of the pyridineethanol derivative and recovering the remaining S form of the pyridineethanol derivative.

In the following, the present invention is described in detail.

First, the method of producing an optically active pyridineethanol derivative [2] by causing an enzyme or enzyme source having asymmetrically reducing activity to act on an acetylpyridine derivative [1] to thereby stereoselectively reduce the same is described in detail.

The acetylpyridine derivative to be used as the substrate in the production method of the invention is represented by the following general formula [1]:

atom and an alkoxy group containing 1 to 12 carbon atoms, among others. $R_3$ and $R_4$ each is preferably a hydrogen or chlorine atom and more preferably a hydrogen atom.

Among the above-mentioned acetylpyridine derivatives of the general formula [1], those represented by the following general formula [3] are particularly preferred:

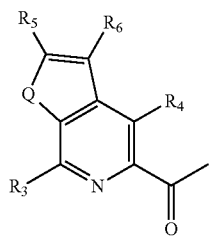

[3]

In the above general formula [3], Q represents an oxygen, sulfur atom or a group of the general formula —N(D)— (in which N is a nitrogen atom and D represents a hydrogen atom or a monovalent protective group). The monovalent protective group is generally well known for protecting the amino group, and includes for example, acetyl, methoxycarbonyl or benzyl. Preferred as Q is an oxygen atom.

$R_3$, $R_4$, $R_5$ and $R_6$ are the same or different and each represents a hydrogen atom, a halogen atom, a hydroxyl group, an alkyl group containing 1 to 12 carbon atoms, which may optionally have a substituent(s), or an alkoxy group containing 1 to 12 carbon atoms, which may optionally have a substituent (s). More specifically, there may be mentioned the same species as those mentioned hereinabove referring to $R_3$ and $R_4$ occurring in the general formula [1].

In a preferred mode of embodiment, the substrate to be used in the production method of the invention is a compound of the general formula [3] in which Q is an oxygen atom, $R_3$ is a hydrogen or chlorine atom, $R_4$ is a hydrogen atoms $R_5$ is a hydrogen atom and $R_6$ is a hydrogen atom or a methyl group.

In a particularly preferred mode of embodiment, the substrate to be used in the production method of the invention is that compound of the general formula [3] in which Q is an oxygen atom and each of $R_3$, $R_4$, $R_5$ and $R_6$ is a hydrogen atom, namely 5-acetylfuro[2,3-c]pyridine.

The above-mentioned acetylpyridine derivatives of the general formula [1] can be readily obtained by production methods known in the art. For example, 5-acetylfuro[2,3-c]pyridine can be synthesized by the method described in EP 911335. 5-Acetyl-7-chlorofuro[2,3-c]pyridine can be prepared by synthesizing 7-chloro-5-(1-hydroxyethyl)furo[2,3-c]pyridine by the method described in J. Org. Chem., 63, 7851(1998) and oxidizing the hydroxyl groups thereof.

The enzyme or enzyme source which can be used in the production method of the invention is derived from a microorganism capable of converting an acetylpyridine derivative [1] to the corresponding optically active pyridineethanol derivative [2]. For instance, cells or a culture of such microorganism, or a material derived therefrom, or the enzyme obtained from such microorganism can be used. These may be used alone or in combination of two or more.

The microorganism capable of converting an acetylpyridine derivative [1] to the corresponding optically active pyridineethanol derivative [2] can be screened out by the method described below. When the acetylpyridine derivative [1] is 5-acetylfuro[2,3-c]pyridine, the screening is carried out as followed. A liquid broth (pH 7; 5 ml; composition, per liter: 40 g of glucose, 3 g of yeast extract, 6.5 g of diammonium hydrogen phosphate, 1 g potassium dihydrogenphosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate, 100 mg of sodium chloride) is placed in each test tube and, after sterilization, aseptically inoculated with the test microorganism, and shake culture is carried out at 30° C. for 2 to 3 days. Thereafter, cells are collected by centrifugation. They are suspended in 1 to 5 ml of a phosphate buffer solution containing 2 to 10% of glucose. The suspension is added to a test tube containing 2.5 to 25 mg of 5-acetylfuro[2,3-c]pyridine placed therein beforehand and the whole is shaken at 30° C. for 2 to 3 days. In this step, the cells collected by centrifugation may also be used in a form dried in a desiccator or with acetone. Further, in reacting such microorganism or a material derived therefrom with 5-acetylfuro[2,3-c]pyridine, oxidized form nicotinamide adenine dinucleotide (hereinafter referred to as "$NAD^+$" for short), reduced form nicotinamide adenine dinucleotide (hereinafter referred to as "NADH" for short), oxidized form nicotinamide adenine dinucleotide phosphate (hereinafter referred to as "$NADP^+$" for short), reduced form nicotinamide adenine dinucleotide phosphate (hereinafter referred to as "NADPH" for short) or the like and a glucose dehydrogenase or formate dehydrogenase may be added. After the conversion reaction, 5 volumes of ethyl acetate is added to the reaction mixture for product extraction. The extract is analyzed by high performance liquid chromatography (column: Chiralpak AS, product of Daicel Chemical Industries; eluate: hexane/ethanol/diethylamine=92/8/0.1; flow rate: 1 ml/min; detection: 254 nm, column temperature: room temperature; elution time: 5-acetylfuro[2,3-c]pyridine 8.8 min, 5-(1-(R)-hydroxyethyl)furo[2,3-c]pyridine 11.7 min, 5-(1-(S)-hydroxyethyl)furo[2,3-c]pyridine 17.5 min).

The microorganism to be used in the practice of the invention may be any of those microorganisms capable of converting an acetylpyridine derivative [1] to the corresponding optically active pyridineethanol derivative [II]. For example, there may be mentioned microorganisms belonging to the genera *Ashbya, Candida, Cryptococcus, Clavispora, Debaryomyces, Dipodascus, Galactomyces, Geotrichum, Guilliermondella, Hanseniaspora, Hansenula, Hyphopichia, Issatchenkia, Kluyveromyces, Kuraishia, Lodderomyces, Metschnikowia, Ogataea, Pachysolen, Pichia, Rhodosporidium, Rhodotorula, Saccharomycopsis, Schwanniomyces, Sporidiobolus, Sporobolomyces, Schizoblastosporion, Stephanoascus, Torulaspora, Trigonopsis, Trichosporon, Willopsis, Yamadazyma, Zygosaccharomyces, Alcaligenes, Bacillus, Brevibacterium, Cellulomonas, Corynebacterium, Jensenia, Ochrobactrum, Pseudomonas, Rhodococcus* and *Tsukamurella*.

In particular when the conversion to a pyridineethanol derivative having the S absolute configuration is intended, microorganisms belonging to the following genera are preferred: *Ashbya, Candida, Cryptococcus, Clavispora, Debaryomyces, Dipodascus, Galactomyces, Geotrichum, Guilliermondella, Hanseniaspora, Hansenula, Hyphopichia, Issatchenkia, Kluyveromyces, Kuraishia, Lodderomyces, Metschnikowia, Ogataea, Pachysolen, Pichia, Rhodosporidium, Rhodotorula, Saccharomycopsis, Schwanniomyces, Sporidiobolus, Sporobolomyces, Schizoblastosporion, Stephanoascus, Torulaspora, Trigonopsis, Trichosporon, Willopsis, Yamadazyma, Zygosaccharomyces, Alcaligenes, Bacillus, Brevibacterium, Cellulomonas,*

Corynebacterium, Jensenia, Ochrobactrum, Pseudomonas, Rhodococcus and Tsukamurella.

When the conversion to a pyridineethanol derivative having the R absolute configuration is intended, microorganisms belonging to the following genera are preferred: Candida, Ogataea, Pichia, Yamadazyma, Brevibacterium and Corynebacterium.

As specific examples to be used for obtaining a pyridineethanol derivative having the S absolute configuration, there may be mentioned, among others, Ashbya gossypii IFO 0560, Candida fennica CBS 6087, Candida guilliermondii IFO 0454, Candida intermedia IFO 0761, Candida krusei IFO 0011, Candida magnoliae IFO 0705, Candida maltosa CBS 5612, Candida versatilis IFO 1908, Candida mogii IFO 0436, Candida norvegensis IFO 1020, Candida parapsilosis IFO 0585, Candida pseudotropicalis IAM 4840, Candida rugosa IFO 0750, Candida oleophila CBS 2219, Candida stellata IFO 0701, Candida tropicalis IFO 0006, Candida bodinii IFO 10574, Candida saitoana IFO 0380, Candida albicans IFO 0759, Candida cariosilignicola IFO 1910, Candida solani IFO 0762, Candida tenuis IFO 0716, Cryptococcus albidus var. albidus IFO 0378, Cryptococcus humicola CBS 1896, Cryptococcus terreus IFO 0727, Clavispora lusitaniae IFO 1019, Debaryomyces hansenii IFO 0082, Debaryomyces marama IFO 0668, Debaryomyces carsonii IFO 0946, Debaryomyces castellii IFO 1359, Dipodascus ovetensis IFO 1201, Dipodascus tetrasperma CBS 765.70, Galactomyces reessii CBS 179.60, Geotrichum candidum CBS178.71, Geotrich fagrans CBS 164.32, Geotrichum candidum CBS 187.67, Guilliermondella selenospora IFO 1850, Hanseniaspora valbyensis IFO 0115, Hansenula polymorpha DL1 AKU 4752, Hyphopichia burtonii IFO 0844, Issatchenkia orientalis IFO 1279, Kluyveromyces lactis IFO 1090, Kluyveromyces thermotolerans IFO 0662, Kuraishia capsulata IFO 0721, Lodderomyces elongisporus IFO 1676, Metschnikowia bicuspidata IFO 1408, Metschnikowia gruessii IFO 0749, Ogataea minuta var. minuta IFO 0975, Ogataea minuta var. nonfermentans IFO1473, Ogataea polymorpha IFO 0799, Pachysolen tannophilus IFO 1007, Pichia rhodanensis IFO 1272, Pichia trehalophila IFO 1282, Pichia wickerhamii IFO 1278, Rhodosporidium diobovatum IFO 0688, Rhodosporidium sphaerocarpum IFO 1438, Rhodosporidium toruloides IFO 0559, Rhodotorula araucariae IFO 10053, Rhodotorula glutinis IFO 1099, Rhodotorula glutinis var. dairenensis IFO 0415, Rhodotorula graminis IFO 0190, Saccharomycopsis fibuligera IFO 0104, Saccharomycopsis malanga IFO 1710, Schwanniomyces occidentalis var. occidentalis IFO 0371, Sporidiobolus johnsonii IFO 6903, Sporobolomyces salmonicolor IAM 12249, Sporobolomyces roseus IFO 1106, Schizoblastosporion kobayasii IFO 1644, Stephanoascus ciferri IFO 1854, Torulaspora globosa IFO 0016, Trigonopsis variabilis IFO 0671, Trichosporon aquatile ATCC 22310, Trichosporon cutaneum IFO 1198, Trichosporon fermentans ATCC 10675, Willopsis saturnus var. suaveolens IFO 0809, Willopsis saturnus var. mrakii IFO 0895, Yamadazyma haplophila IFO 0947, Zygosaccharomyces bailii IFO 0488, Zygosaccharomyces rouxii IFO 0493, Alcaligenes xylosoxidans IFO 13495, Alcaligenes xylosoxidans subsp. dentrificans IFO 12669, Bacillus megaterium, Bacillus amyloliquefaciens IFO 3022, Brevibacterium incertum IFO 12145, Cellulomonas fimi IAM 12107, Corynebacterium sp. ATCC 21245, Jensenia canicruria IFO 13914, Ochrobactrum sp. IFO 12950, Pseudomonas stutzeri IFO 13596, Pseudomonas chlororaphis IFO 3904, Pseudomonas mendocina IFO 14162, Rhodococcus erythropolis IFO 12320, Rhodococcus rhodochrous IFO 3338, and Tsukamurella paurometabola IFO 12160.

For obtaining a pyridineethanol derivative having the R absolute configuration, there can be mentioned Candida etchellsii IFO 1942, Candida lactiscondensi IFO 1286, Candida maris IFO 10003, Ogataea wickerhamii IFO 1706, Pichia farinosa IFO 0602, Pichia membranae faciens IFO 0460, Pichia naganishii IFO 1670, Yamadazyma farinosa IFO 0534, Brevibacterium iodinam IFO 3558 and Corynebacterium acetoacidophilum ATCC 21476, among others.

These microorganisms can be obtained from stock cultures readily available or purchasable or can be isolated from the natural world. It is also possible to obtain strains having favorable properties for this reaction by causing mutation of these microorganisms.

In culturing these microorganisms, any of the media containing nutrient sources assimilable by these microorganisms can generally be used. For example, use may be made of ordinary media prepared by mixing and incorporating appropriate amounts of carbon sources, for example saccharides such as glucose, sucrose, maltose, etc., organic acids such as lactic acid, acetic acid, citric acid, propionic acid, etc., alcohols such as ethanol, glycerol, etc., hydrocarbons such as paraffins, fats and oils such as soybean oil, rapeseed oil, etc., or mixtures of these; nitrogen sources such as ammonium sulfate, ammonium phosphate, urea, yeast extract, meat extract, peptone, corn steep liquor, etc.; and, further, other nutrients sources, for example other inorganic salts, vitamins, etc. The medium to be used may be selected from among these media according to the microorganism to be used.

The culture of the microorganism can be generally carried out under ordinary conditions, preferably at a pH of 4.0 to 9.5 and a temperature within the range of 20° C. to 45° C. under aerobic conditions for 10 to 96 hours, for instance. In reacting the microorganism with an acetylpyridine derivative [1], the culture broth containing cells of the microorganism can generally be used as it is. The culture broth may also be used in a concentrated form. In cases a certain component in the culture broth adversely affects the reaction, cells or a material derived therefrom as obtained by centrifugation and/or other treatments of the culture broth may also be used.

The material derived from cells of the microorganism is not particularly restricted but includes, among others, dried cells obtained by dehydration treatment with acetone or diphosphorus pentoxide or by drying utilizing a desiccator or electric fan, materials derived by surfactant treatment, materials derived by lysozyme treatment, immobilized cells and cell-free extract preparations derived from disruption of cells. It is also possible to purify an enzyme catalyzing the asymmetric reduction reaction from the culture and use the same.

In carrying out the reduction reaction in accordance with the invention, the substrate acetylpyridine derivative [1] may be added all at once at the beginning of the reaction or in divided portions with the progress of the reaction. The temperature during the reaction is generally 10 to 60° C., preferably 20 to 40° C., and the pH during the reaction is within the range of 2.5 to 9, preferably 5 to 9. The amount of the enzyme or enzyme source in the reactant mixture may be adequately selected according to the ability thereof to reduce the substrate. The substrate concentration in the reactant mixture is preferably 0.01 to 50% (w/v), more preferably 0.1 to 30% (w/v). The reaction is generally carried out with shaking or with aeration and stirring. The reaction time is adequately selected according to the substrate concentration, enzyme or enzyme source amount and other reaction conditions. Generally, it is preferred to select such reaction conditions so that the reaction may be complete in 2 to 168 hours.

For promoting the reduction reaction according to the invention, the addition, in an amount of 0.5 to 30%, of such an energy source as glucose, ethanol or isopropanol to the reactant mixture is preferred since better results are obtained.

The reaction can also be promoted by adding a coenzyme generally required for biochemical reduction reactions, such as NADH and NADPH. In this case, specifically, such coenzyme is directly added to the reactant mixture.

Further, for promoting the reduction reaction, it is preferred to carry out the reaction in the presence of an enzyme reducing $NAD^+$ and/or $NADP^+$ to the respective reduced forms and a substrate for the reduction, since better results are obtained. For example, a glucose dehydrogenase can be caused to exist as the enzyme for the reduction to the reduced form and glucose can be caused to exist as the substrate for reduction, or a formate dehydrogenase can be caused to exist as the enzyme for the reduction to the reduced form and formic acid can be caused to exist as the substrate for reduction.

It is also effective to add a surfactant such as Triton (product of Nakalai Tesque), Span (product of Kanto Chemical) or Tween (product of Nakalai Tesque) to the reactant mixture. A water-insoluble organic solvent such as ethyl acetate, butyl acetate, isopropyl ether, toluene and hexane may be added to the reactant mixture for the purpose of avoiding the inhibition of the reaction by the acetylpyridine derivative [1] and/or optically active pyridineethanol derivative [2]. For increasing the solubility of the acetylpyridine derivative [1], a water-soluble organic solvent, such as methanol, ethanol, acetone, tetrahydrofuran and dimethyl sulfoxide may also be added.

In the following, the enzyme, the DNA coding for said enzyme, the recombinant vector containing said DNA and the transformant having said recombinant vector according to the invention are described in detail.

The enzyme of the invention has the following physical and chemical properties (1) to (3):

(1) Activity: It stereoselectively reduces 5-acetylfuro[2,3-c] pyridine, in the presence of NADH as a coenzyme, to give 5-(1-(R)-hydroxyethyl)furo[2,3-c]pyridine;

(2) Specificity: It has reducing ability against ketones and aldehydes but is very low in reducing activity against carbocyclic ketones and the α-position keto group of α-keto acids;

(3) Molecular weight: It shows a molecular weight of about 60,000 in gel filtration analysis and a molecular weight of about 29,000 in SDS polyacrylamide electrophoresis.

Preferably, the enzyme has the following physical and chemical properties (4) to (6) in addition to the physical and chemical properties (1) to (3):

(4) Optimal temperature: 50° C. to 55° C.;

(5) Optimal pH: 5.0 to 6.0;

(6) Inhibitor: It is inhibited by the mercury ion.

In the practice of the invention, the reducing activity of the enzyme is determined by carrying out the reaction in 3.0 ml of a reactant mixture containing 1 mM substrate, 0.25 mM coenzyme NADH, 0.3% (vol/vol) dimethyl sulfoxide and an enzyme solution in 100 mM phosphate buffer (pH 6.5) at 30° C. for 3 minutes and then measuring the reduction in absorbance at 340 nm.

The term "very low in reducing activity" referring to the specificity means that when the reducing activity against 5-acetylfuro[2,3-c]pyridine is taken as 100%, the reducing activity against the substrate in question is not more than 10%. The term "carbocyclic ketones" means ketones, such as cyclohexanone and cyclopentanone, derived from alicyclic compounds by substituting —C(=O)— for a ring constituent —$CH_2$— thereof.

The molecular weight is determined by gel filtration analysis using a TSK-G 3000 SW column (7.8 mm I.D.×30 cm) (product of Tosoh Corp.). It is calculated based on the relative elution times of standard proteins. The subunit molecular weight is calculated based on the relative mobilities of standard proteins as determined by 20% SDS-polyacrylamide gel electrophoresis.

The optimal pH and optimal temperature for the enzyme are determined, for example, by measuring the reducing activity while varying the reaction pH and reaction temperature of the reducing activity measuring system.

The inhibitor is found out, for example, by measuring the reducing activities of various compounds added to the reducing activity measuring system.

The microorganism to be used as a source of the enzyme of the invention may be any of the microorganisms having an enzyme capable of stereoselectively reducing 5-acetylfuro[2,3-c]pyridine to give 5-(1-(R)-hydroxyethyl)furo[2,3-c]pyridine. It may be a wild species or a mutant and, further, a recombinant microorganism derived by a genetic engineering technique such as cell fusion or gene manipulation. Preferably, a microorganism belonging to the genus Candida is used. The species *Candida maris* is more preferred, and the strain *Candida maris* IFO 10003 is particularly preferred.

In the following, an example of the method of preparing an enzyme of the invention from a microorganism having the enzyme capable of stereoselectively reducing 5-acetylfuro[2,3-c]pyridine to give 5-(1-(R)-hydroxyethyl)furo[2,3-c]pyridine is described. It is to be noted, however, that this example is by no means limitative of the scope of the invention. A crude enzyme solution can be obtained by cultivating, in an appropriate medium, a microorganism having an enzyme capable of stereoselectively reducing 5-acetylfuro[2,3-c]pyridine to give 5-(1-(R)-hydroxyethyl) furo[2,3-c]pyridine, collecting cells from the culture broth by centrifugation, suspending the cells in an appropriate buffer solution, disrupting or lysing the cells by physical means such as glass beads or by biochemical means such as an enzyme and, further, removing the solid matter from the solution by centrifugation. Alternately, a crude enzyme solution can also be obtained from the culture broth by the same purification procedure as mentioned above. Further, this crude enzyme solution can be purified by techniques generally used by those skilled in the art, for example precipitation with ammonium sulfate, dialysis and chromatography, used either singly or in combination. The chromatography includes hydrophobic chromatography, ion exchange chromatography and gel filtration chromatography and these techniques may be used singly or in combination.

The enzyme of the invention may be a natural enzyme obtained from a microorganism as mentioned above, or a recombinant enzyme. As a natural enzyme, there may be mentioned an enzyme comprising the amino acid sequence shown under SEQ ID NO:1 in the sequence listing.

The enzyme of the invention may also be an enzyme comprising an amino acid sequence derived from the amino acid sequence shown under SEQ ID NO:1 in the sequence listing by deletion, substitution and/or addition of one or several amino acids and capable of stereoselectively reducing 5-acetylfuro[2,3-c]pyridine to give 5-(1-(R)-hydroxyethyl)furo[2,3-c]pyridine. The terms "deletion, substitution and/or addition of one or several amino acids" mean that such a number of amino acids as capable of being deleted, substituted and/or added by a method well known in the art, for example site-specific mutagenesis, are deleted, substituted and/or added. The terms "capable of stereoselectively reducing 5-acetylfuro[2,3-c]pyridine to give 5-(1-(R)-hydroxyethyl)furo[2, 3-c]pyridine" mean that when the enzyme is reacted with 5-acetylfuro[2,3-c]pyridine, 5-(1-(R)-hydroxyethyl)furo[2,3-c]pyridine is formed in a yield of not less than 10%, preferably not less than 40%, particularly preferably not less than 60%, of the yield obtained with the enzyme comprising the amino acid sequence shown under SEQ ID NO:1 in the sequence listing. For determining such yield, the above-mentioned high performance liquid chromatography is used.

Once an enzyme has been obtained in a purified form, a DNA coding for the enzyme can be obtained by a method well known in the art. By introducing this DNA into another microorganism and cultivating the resulting recombinant microorganism, it is possible to produce the relevant enzyme source usable in the production method of the invention in large amounts.

In the following, an example of the process for obtaining a DNA coding for an enzyme of the invention is described. Of course, the present invention is not restricted to this process. First, the enzyme purified is digested with an appropriate endopeptidase, digested fragments are purified by reversed phase HPLC and partial amino acid sequences thereof are determined by means of a protein sequencer. Based on the partial amino acid sequences, PCR (polymerase chain reaction) primers are synthesized. Then, chromosomal DNA is prepared from the microorganism, which is the source of the enzyme-encoding DNA, by a conventional method of DNA isolation, for example the Hereford method (Cell, 18, 1261 (1979)). Part of the enzyme-encoding DNA (core sequence) is amplified by performing PCR using the above PCR primers with the above chromosomal DNA as a template, and that part is sequenced. The sequencing can be carried out by the dideoxy chain termination method or like method using the ABI 373A DNA sequencer (Applied Biosystems), for instance. For revealing the base sequence in regions adjacent to the core sequence, the microbial chromosomal DNA is digested with a restriction enzyme having no recognition sequence in the core sequence and the resulting DNA fragment is allowed to self-circulize using T4 ligase to give a template DNA for inverse PCR (Nucleic Acids Res. 16, 8186 (1988)). Then, based on the core sequence, primers to serve as the initiation points for DNA synthesis toward the outsides of the core sequence are synthesized, and the regions neighboring the core sequence are amplified by inverse PCR. By revealing the base sequences of the thus-obtained DNAs, it is possible to reveal the DNA sequence of the whole coding region for the desired enzyme. Once the DNA sequence in question has been revealed, the DNA coding for the enzyme of the invention can be obtained from that microbial chromosomal DNA by PCR, for instance.

The DNA encoding the enzyme of the invention is inserted into a vector and the resulting recombinant vector is introduced into a host, whereupon the enzyme gene can be expressed in the resulting transformant. The vector to be used for this purpose may be any, of those allowing the expression of the enzyme gene in an appropriate host. As such vector, there may be mentioned plasmid vectors, phage vectors and cosmid vectors, among others. Shuttle vectors capable of gene exchange with some other host may also be used. Such vectors each contain operatively joined regulator elements such as a promoter (lac UV5 promoter, trp promoter, trc promoter, tac promoter, lpp promoter, tufB promoter, recA promoter, pL promoter) and can be used as an expression vector containing an expression unit operatively linked to the DNA of the invention. Thus, for example, pUCNT (WO 94/03613) and the like can suitably be used.

The term "regulatory factors" as used herein means base sequences including a functional promoter, and if necessary related transcription elements (e.g. enhancer, CCAAT box, TATA box, SPI site, etc.).

The term "operatively joined" means that the DNA and various regulator elements, such as a promoter, enhancer, etc., are joined together so that they can operate in a host cell to cause gene expression. It is well known in the art that the regulator elements may vary in type and species according to the host.

The host into which the recombinant vector containing the DNA of the invention includes bacteria, yeasts, filamentous fungi, plant cells, animal cells, etc. *Escherichia coli* is most preferred, however. The DNA of the invention can be introduced into the host in the conventional manner. When *Escherichia coli* is used as the host cells, the DNA of the invention can be introduced thereinto by the calcium chloride method, for instance.

For stereoselectively reducing an acetylpyridine derivative [1] using the enzyme or transformant of the invention to give the corresponding pyridineethanol derivative having the R absolute configuration, particularly preferably for stereoselectively reducing 5-acetylfuro[2,3-c]pyridine to give 5-(1-(R)-hydroxyethyl)furo[2,3-c]pyridine, NADH is required as a coenzyme. While the reduction can be carried out by adding a required amount of NADH to the reaction system, the amount of the expensive coenzyme can be markedly reduced by carrying out the reaction using the enzyme of the invention in combination with a coenzyme regeneration system, namely using an enzyme capable of converting the oxidized form of that enzyme ($NAD^+$) to the reduced form (NADH) (hereinafter referred to as coenzyme regeneration ability) together with the substrate thereof. As the enzyme having coenzyme regeneration ability, use may be made of hydrogenase, formate dehydrogenase, alcohol dehydrogenase, glucose-6-phosphate dehydrogenase and glucose dehydrogenase, among others. Glucose dehydrogenase and formate dehydrogenase are judiciously used, however.

Such reaction can be carried out by adding the coenzyme regeneration system to the asymmetric reduction reaction system. When a transformant resulting from the transformation with both the DNA coding for the enzyme of the invention and a DNA coding for glucose dehydrogenase is used, the reaction can efficiently be carried out without adding any enzyme having coenzyme regeneration ability as separately prepared. Such transformant can be produced by inserting a DNA coding for the enzyme of the invention and a DNA coding for glucose dehydrogenase into one and the same vector and introducing the recombinant vector into a host, or by inserting each of two DNAs into two vectors differing in incompatibility group separately and introducing these into one and the same host. Thus, a transformant having a recombinant vector containing a DNA coding for the enzyme of the invention and a DNA coding for glucose dehydrogenase, or a transformant having a first recombinant vector containing a DNA coding for the enzyme of the invention and a second recombinant vector containing a DNA coding for glucose dehydrogenase can be used.

In cases where the enzyme or transformant of the invention has coenzyme regeneration ability, the reaction for regeneration of NADH can be conducted simultaneously by adding a substrate for that regeneration to the reaction system and, thus, the amount of the expensive coenzyme to be used can be markedly reduced without supplementary adding another enzyme having coenzyme regeneration ability. For example, when the enzyme or transformant of the invention has isopropanol oxidizing activity, it becomes possible to carry out the regeneration of NADH by adding isopropanol to the reduction system.

The production of an optically active pyridineethanol derivative [2] from an acetylpyridine derivative [1] using the transformant of the invention, in particular the production of 5-(1-(R)-hydroxyethyl)furo[2,3-c]pyridine from 5-acetyl-furo[2,3-c]pyridine, can be performed in the following manner. Such production, however, is not limited to the following process. First, the substrate 5-acetylfuro[2,3-c]pyridine [1], a coenzyme such as $NAD^+$ and a culture of the transformant or a material derived therefrom or the like are added to an appropriate solvent, and the reaction is allowed to proceed at an adjusted pH with stirring. This reaction is carried out at a temperature of 10 to 70° C. and the pH of the reaction mixture is maintained at 4 to 10 during the reaction. The reaction can be conducted either batchwise or continuously. In the case of batchwise reaction, the reaction substrate can be added in a charge concentration of 0.1% to 70% (w/v). The material derived from the transformant, so referred to herein, includes, among others, crude enzyme solutions, cultured microbial cells, lyophilized microbial cells, acetone-dried microbial cells, triturated modifications thereof, and mixtures of these. Furthermore, the enzyme itself or microbial cells themselves may be used in a form immobilized by conventional means. Further, when, in carrying out the reaction, the transformant employed can produce both the enzyme of the invention and glucose dehydrogenase, the addition amount of coenzyme can be markedly reduced by further adding glucose to the reaction system.

Now, the method of producing a pyridineethanol derivative having the S absolute configuration by reacting the above enzyme and/or transformant with a pyridineethanol derivative to thereby preferentially oxidizing the pyridineethanol derivative having the R absolute configuration and recovering the remaining pyridineethanol derivative having the S absolute configuration is described in detail.

The pyridineethanol derivative to be used as the substrate in the production method according to the invention is represented by the general formula [5]:

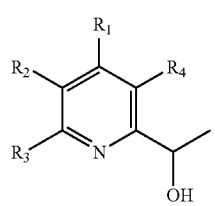

In the above general formula [5], $R_1$ and $R_2$ are as defined above in relation to the general formula [1]. Five-membered monocyclic heterocycles are preferred among others, a substituted or unsubstituted furan ring is more preferred and a furan ring is particularly preferred.

$R_3$ and $R_4$ are also as defined as above referring to the general formula [1]. A hydrogen atom or chlorine atom is preferred and a hydrogen atom is more preferred.

The pyridineethanol derivative [5] is not particularly restricted but has an optical purity of less than 100%. It may be entirely a racemate or have a certain degree of optical purity.

Among the pyridineethanol derivatives [5], particularly preferred species are represented by the general formula [7]:

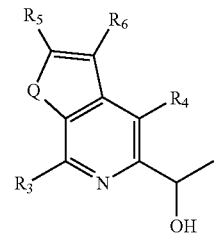

In the above general formula [7], Q is as defined above in reference to the general formula [3]. An oxygen atom is preferred as Q. $R_3$, $R_4$, $R_5$ and $R_6$ are also as defined above referring to the general formula [3].

In a preferred embodiment, the substrate to be used in the production method of the invention is a compound represented by the general formula [7] in which Q is an oxygen atom, $R_3$ is a hydrogen atom or chlorine atom, $R_4$ is a hydrogen atom, $R_5$ is a hydrogen atom and $R_6$ is a hydrogen atom or a methyl group.

In a particularly preferred embodiment, the substrate to be used in the production method of the invention is a compound represented by the general formula [7] in which Q is an oxygen atom, $R_3$, $R_4$, $R_5$ and $R_6$ each is a hydrogen atom, namely 5-(1-hydroxyethyl)furo[2,3-c]pyridine.

The pyridineethanol derivatives represented by the general formula [5] can be readily obtained by production methods known in the art. For example, 5-(1-hydroxyethyl)furo[2,3-c]pyridine can be synthesized by the method described in EP 911335.

For preferentially oxidizing an R-configuration pyridineethanol derivative by reacting the pyridineethanol derivative [5] with the enzyme or transformant of the invention, $NAD^+$ is required as a coenzyme. While the reaction can be carried out by adding a required amount of $NAD^+$ to the reaction system, the required amount of the expensive coenzyme can be markedly reduced by carrying out the reaction by using an enzyme capable of converting the reduced form of the coenzyme to the oxidized form and a substrate for that enzyme in combination with the enzyme of the invention. A microorganism or a material derived therefrom, which contains an enzyme capable of converting the reduced form of the coenzyme to the oxidized form may also be used. Useful as the enzyme capable of converting the reduced form of the coenzyme to the oxidized form are, for example, NADH oxidase and NADH dehydrogenase.

In cases where the enzyme or transformant of the invention has $NAD^+$ regeneration ability, the $NAD^+$ regeneration reaction can be conducted simultaneously by adding a substrate for that regeneration to the reaction system. In that case, the amount of the expensive coenzyme can be markedly reduced without particularly adding another enzyme having NAD$^+$ regeneration ability. For example, when the enzyme or transformant of the invention has acetone reducing activity, the addition of acetone to the reaction system enables the regeneration of NAD$^+$.

Further, when the transformant of the invention is used, the reaction can proceed owing to the NAD$^+$ occurring within the microbial cells and the NADH produced upon the reduction of NAD$^+$ is reoxidized within the microbial cells, hence the reaction can be conducted without particularly adding the coenzyme and an enzyme having NAD$^+$ regeneration ability.

The method of recovering the optically active pyridineethanol derivative obtained by any of the above-mentioned methods is not particularly restricted but the optically active pyridineethanol derivative can be readily obtained, in a highly pure form, by extracting the product from the reaction mixture, directly or after separation of microbial cells, with a solvent such as ethyl acetate, toluene, tert-butyl methyl ether and hexane, dehydrating the extract and purifying the product by distillation, crystallization, silica gel column chromatography, etc.

BRIEF DESCRIPTION OF THE DRAWINGS

FIG. 1 shows the DNA base sequence, SEQ ID NO. 2, determined in Example 21 and the amino acid sequence deduced therefrom, SEQ ID NO. 1.

BEST MODES FOR CARRYING OUT THE INVENTION

Figure 2:
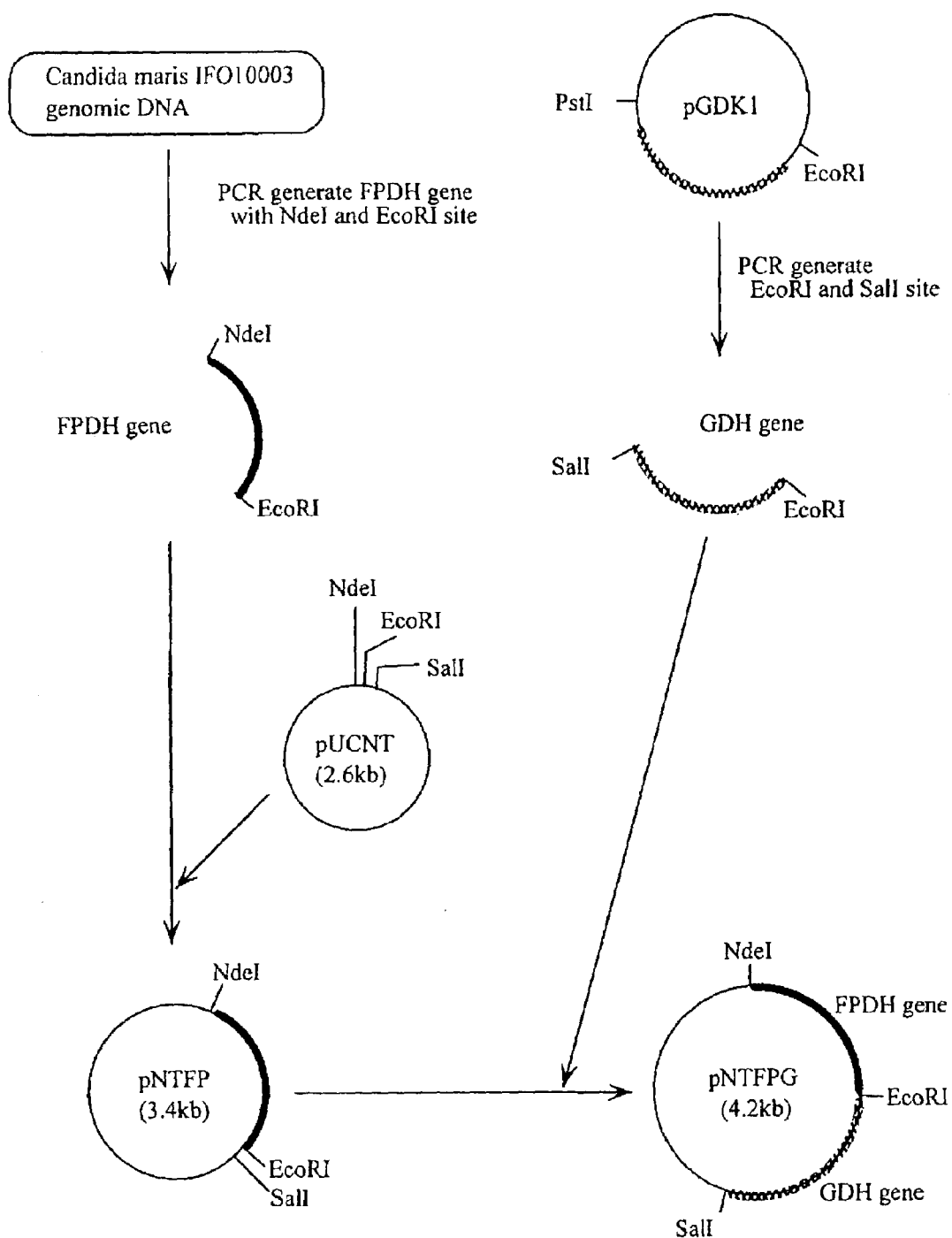
FIG. 2 shows a method of constructing the recombinant vector pNTFP of Example 22 and the recombinant vector pNTFPG of Example 23 and the structures of these.

The following examples illustrate the present invention in further detail. These examples are, however, by no means limitative of the scope of the invention. In the following description, "%" means "% by weight" unless otherwise specified.

EXAMPLE 1

Asymmetric Reduction of 5-acetylfuro[2,3-c]pyridine Using Various Microorganisms A liquid broth (pH 7) comprising 40 g of glucose, 3 g of yeast extract, 6.5 g of diammonium hydrogen phosphate, 1 g of potassium dihydrogen-phosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride, per liter, was distributed in 5-ml portions into large size test tubes and steam-sterilized at 120° C. for 20 minutes. These liquid broth portions were each aseptically inoculated with one loopful of one of the microorganisms listed in Table 1 and Table 2, and shake culture was carried out at 30° C. for 24 to 72 hours. After cultivation, 0.5 ml of each culture was centrifuged and the cells collected were suspended in 0.5 ml of 100 mM phosphate buffer (pH 6.5) containing 8% of glucose. This cell suspension was added to a test tube containing 5 mg of 5-acetylfuro[2,3-c]pyridine placed therein in advance, and the reaction was allowed to proceed at 30° C. for 26 hours. After reaction, 5 ml of ethyl acetate was added to each reaction mixture and, after mixing up, a portion of the organic phase was analyzed under the following HPLC conditions.

[HPLC Analysis Conditions]

Column: Chiralpak AS, product of Daicel Chemical Industries;

eluent: hexane/ethanol/diethylamine=92/8/0.1; flow rate: 1 ml/min; detection: 254 nm; column temperature: room temperature; elution time: 5-acetylfuro[2,3-c]pyridine 8.8 minutes, 5-(1-(R)-hydroxyethyl)furo[2,3-c]pyridine 11.7 minutes, 5-(1-(S)-hydroxyethyl)furo[2,3-c]pyridine 17.5 minutes.

The yield, optical purity and absolute configuration of the product 5-(1-hydroxyethyl)furo[2,3-c]pyridine per reaction mixture are shown in Table 1 or Table 2.

TABLE 1

| Microorganism | Yield (mg/ml) | Optical purity (% e.e.) | Absolute configuration |
|---|---|---|---|
| Ashbya gossypii IFO 0560 | 0.17 | 95.6 | S |
| Candida fennica CBS 6087 | 0.43 | 69.7 | S |
| Candida guilliermondii IFO 0454 | 0.86 | 95.3 | S |
| Candida intermedia IFO 0761 | 2.81 | 99.2 | S |
| Candida krusei IFO 0011 | 0.12 | 100.0 | S |
| Candida magnoliae IFO 0705 | 2.41 | 59.4 | S |
| Candida maltosa CBS 5612 | 7.43 | 99.9 | S |
| Candida versatilis IFO 1908 | 0.11 | 94.5 | S |
| Candida mogii IFO 0436 | 2.73 | 99.1 | S |
| Candida norvegensis IFO 1020 | 0.18 | 100.0 | S |
| Candida parapsilosis IFO 0585 | 5.86 | 99.8 | S |
| Candida pseudotropicalis IAM 4840 | 0.32 | 95.6 | S |
| Candida rugosa IFO 0750 | 0.12 | 91.9 | S |
| Candida oleophila CBS 2219 | 0.72 | 79.8 | S |
| Candida stellata IFO 0701 | 0.11 | 100.0 | S |
| Candida tropicalis IFO 0006 | 6.17 | 99.9 | S |
| Candida bodinii IFO 10574 | 0.21 | 90.5 | S |
| Candida saitoana IFO 0380 | 0.32 | 89.0 | S |
| Candida albicans IFO 0759 | 4.12 | 98.1 | S |
| Candida cariosilignicola IFO 1910 | 1.44 | 100.0 | S |
| Candida solani IFO 0762 | 0.32 | 94.4 | S |
| Candida tenuis IFO 0716 | 0.36 | 95.1 | S |
| Cryptococcus albidus var albidus IFO 0378 | 2.37 | 99.3 | S |
| Cryptococcus humicola CBS 1896 | 0.33 | 87.6 | S |
| Cryptococcus terreus IFO 0727 | 0.26 | 83.3 | S |
| Clavispora lusitaniae IFO 1019 | 0.60 | 98.4 | S |
| Debaryomyces hansenii IFO 0082 | 0.48 | 94.2 | S |
| Debaryomyces marama IFO 0668 | 0.12 | 64.8 | S |
| Debaryomyces carsonii IFO 0946 | 0.40 | 83.8 | S |
| Debaryomyces castellii IFO 1359 | 0.70 | 81.6 | S |
| Dipodascus ovetensis IFO 1201 | 6.81 | 97.2 | S |
| Dipodascus tetrasperma CBS 765.70 | 2.77 | 93.7 | S |
| Galactomyces reessii CBS 179.60 | 0.42 | 86.9 | S |
| Geotrichum candidum CBS 178.71 | 9.24 | 98.8 | S |
| Geotrichum fragrans CBS 164.32 | 3.03 | 98.8 | S |
| Geotrichum candidum CBS 187.67 | 0.26 | 64.2 | S |
| Guilliermondell selenospora IFO 1850 | 0.34 | 56.9 | S |
| Hanseniaspora valbyensis IFO 0115 | 0.36 | 92.9 | S |
| Hansenula polymorpha DL1 AKU 4752 | 0.38 | 95.2 | S |
| Hyphopichia burtonii IFO 0844 | 6.25 | 96.7 | S |
| Issatchenkia orientalis IFO 1279 | 0.20 | 97.5 | S |
| Kluyveromyces lactis IFO 1090 | 0.15 | 83.0 | S |
| Kluyveromyces thermotolerans IFO 0662 | 0.98 | 94.3 | S |

TABLE 2

| Microorganism | Yield (mg/ml) | Optical purity (% e.e.) | Absolute configuration |
|---|---|---|---|
| *Kuraishia capsulata* IFO 0721 | 0.78 | 98.8 | S |
| *Lodderomyces elongisporus* IFO 1676 | 3.05 | 99.3 | S |
| *Metschnikowia bicuspidata* IFO 1408 | 0.15 | 72.8 | S |
| *Metschnikowia gruessii* IFO 0749 | 0.28 | 50.7 | S |
| *Ogataea minuta* var. *minuta* IFO 0975 | 0.59 | 98.4 | S |
| *Ogataea minuta* var. *nonfermentans* IFO 1473 | 0.22 | 100.0 | S |
| *Ogataea polymorpha* IFO 0799 | 0.16 | 94.7 | S |
| *Pachysolen tannophilus* IFO 1007 | 0.26 | 67.3 | S |
| *Pichia rhodanensis* IFO 1272 | 0.26 | 97.9 | S |
| *Pichia trehalophila* IFO 1282 | 0.63 | 98.7 | S |
| *Pichia wickerhamii* IFO 1278 | 0.47 | 98.0 | S |
| *Rhodsporidium diobovatum* IFO 0688 | 0.42 | 100.0 | S |
| *Rhodsporidium sphaerocarpum* IFO 1438 | 4.13 | 100.0 | S |
| *Rhodsporidium toruloides* IFO 0559 | 6.45 | 99.9 | S |
| *Rhodotorula araucariae* IFO 10053 | 2.52 | 74.6 | S |
| *Rhodotorula glutinis* IFO 1099 | 2.54 | 100.0 | S |
| *Rhodotorula glutinis* var. *dairenensis* IFO 0415 | 1.34 | 100.0 | S |
| *Rhodotorula graminis* IFO 0190 | 1.95 | 99.5 | S |
| *Saccharomycopsis fibuligera* IFO 0104 | 1.28 | 100.0 | S |
| *Saccharomycopsis malanga* IFO 1710 | 0.61 | 100.0 | S |
| *Schwanniomyces occidentalis* var. *occidentalis* IFO 0371 | 0.26 | 94.3 | S |
| *Sporidiobolus johnsonii* IFO 6903 | 5.58 | 99.2 | S |
| *Sporobolomyces salmonicolor* IAM 12249 | 2.99 | 97.4 | S |
| *Sporobolomyces roseus* IFO 1106 | 0.34 | 85.1 | S |
| *Schizoblastosporion kobayasii* IFO 1644 | 0.46 | 79.4 | S |
| *Stephanoascus ciferrii* IFO 1854 | 0.50 | 95.2 | S |
| *Torulaspora glohosa* IFO 0016 | 0.95 | 42.2 | S |
| *Trigonopsis variabilis* IFO 0671 | 0.95 | 48.7 | S |
| *Trichosporon aquatile* ATCC 22310 | 0.25 | 70.3 | S |
| *Trichosporon cutaneum* IFO 1198 | 0.16 | 100.0 | S |
| *Trichosporon fermentans* ATCC 10675 | 2.45 | 85.2 | S |
| *Williopsis saturnus* var. *suaveolens* IFO 0809 | 0.11 | 83.3 | S |
| *Willopsis saturnus* var. *mrakii* IFO 0895 | 3.05 | 98.5 | S |
| *Yamadazyma haplophila* IFO 0947 | 1.19 | 96.8 | S |
| *Zygosaccharomyces bailii* IFO 0488 | 0.10 | 61.6 | S |
| *Zygosaccharomyces rouxii* IFO 0493 | 0.17 | 47.0 | S |
| *Candida etchellsii* IFO 1942 | 0.24 | 87.0 | R |
| *Candida lactis-condensi* IFO 1286 | 1.28 | 96.5 | R |
| *Candida maris* IFO 10003 | 7.08 | 98.4 | R |
| *Ogataea wickerhamii* IFO 1706 | 7.68 | 77.6 | R |
| *Pichia farinosa* IFO 0602 | 7.15 | 39.2 | R |
| *Pichia membranaefaciens* IFO 0460 | 0.11 | 77.3 | R |
| *Pichia naganishii* IFO 1670 | 0.33 | 22.3 | R |
| *Yamadazyma farinosa* IFO 0534 | 3.12 | 97.4 | R |

EXAMPLE 2

Asymmetric Reduction of 5-acetylfuro[2,3-c]pyridine Using Various Microorganisms A liquid broth (pH 7) comprising 10 g meat extract, 10 g peptone, 5 g of yeast extract and 3 g sodium chloride, per liter, was distributed in 5-ml portions into large size test tubes and steam-sterilized at 120° C. for 20 minutes. These liquid broth portions were each aseptically inoculated with one loopful of one of the microorganisms listed in Table 3, and shake culture was carried out at 30° C. for 24 to 72 hours. After cultivation, 2 ml of each culture was centrifuged and the cells collected were suspended in 0.5 ml of 100 mM phosphate buffer (pH 6.5) containing 8% of glucose. This cell suspension was added to a test tube containing 2.5 mg of 5-acetylfuro[2,3-c]pyridine placed therein in advance, and the reaction was allowed to proceed at 30° C. for 26 hours. After reaction, the reaction mixture was analyzed in the same manner as in Example 1. The yield, optical purity and absolute configuration of the product 5-(1-hydroxyethyl)furo[2,3-c]pyridine per reaction mixture are shown in Table 3.

TABLE 3

| Microorganism | Yield (mg/ml) | Optical purity (% e.e.) | Absolute configuration |
|---|---|---|---|
| *Alcaligenes xylosoxidans* IFO 13495 | 0.05 | 93.1 | S |
| *Alcaligenes xylosoxidans* subsp. *dentrificans* IFO 12669 | 0.13 | 97.3 | S |
| *Bacillus megaterium* | 0.13 | 94.6 | S |
| *Bacillus amyloliquefaciens* IFO 3022 | 0.10 | 97.7 | S |
| *Brevibacterium incertum* IFO 12145 | 0.20 | 98.4 | S |
| *Cellulomonas fimi* IAM 12107 | 1.16 | 91.5 | S |
| *Corynebacterium* sp. ATCC 21245 | 0.26 | 57.3 | S |
| *Jensenia canicruria* IFO 13914 | 4.91 | 98.6 | S |
| *Ochrobactrum* sp. IFO 12950 | 0.68 | 98.9 | S |
| *Pseudomonas stutzeri* IFO 13596 | 3.99 | 99.9 | S |
| *Pseudomonas chlororaphis* IFO 3904 | 0.21 | 95.9 | S |
| *Pseudomonas mendocina* IFO 14162 | 0.65 | 99.2 | S |
| *Rhodococcus erythropolis* IFO 12320 | 0.13 | 68.5 | S |
| *Rhodococcus rhodochrous* IFO 3338 | 0.10 | 85.8 | S |
| *Tsukamurella paurometabola* IFO 12160 | 0.16 | 98.7 | S |
| *Brevibacterium iodinam* IFO 3558 | 0.15 | 42.3 | R |
| *Corynebacterium acetoacidophilum* ATCC 21476 | 0.12 | 40.9 | R |

COMPARATIVE EXAMPLE 1

Asymmetric Reduction of 5-acetylfuro[2,3-c]pyridine Using Various Microorganisms A liquid broth (pH 7) comprising 40 g of glucose, 3 g of yeast extract, 6.5 g of diammonium hydrogen phosphate, 1 g of potassium dihydrogen-phosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride, per liter, was distributed in 5-ml portions into large size test tubes and steam-sterilized at 120° C. for 20 minutes. These liquid broth portions were each aseptically inoculated with one loopful of one of the microorganisms listed in Table 4, and shake culture was carried out at 30° C. for 24 to 72 hours. After cultivation, 2 ml of each culture was centrifuged and the cells collected were suspended in 0.5 ml of 100 mM phosphate buffer (pH 6.5) containing 8% of glucose. This cell suspension was added to a test tube containing 2.5 mg of 5-acetylfuro[2,3-c]pyridine placed therein in advance, and the reaction was allowed to proceed at 30° C. for 26 hours. After reaction, the reaction mixture was analyzed in the same manner as in Example 1. The yield, optical purity and absolute configuration of the product 5-(1-hydroxyethyl)furo[2,3-c]pyridine per reaction mixture are shown in Table 4.

TABLE 4

| Microorganism | Yield (mg/ml) | Optical purity (% e.e.) | Absolute configuration |
|---|---|---|---|
| *Saccharomyces cerevisiae* IFO 0258 | 0.00 | — | — |
| *Saccharomyces cerevisiae* ATCC 9017 | 0.01 | — | — |

From the above results, it is evident that *Saccharomyces cerevisiae* known to be capable of converting the monocyclic acetylpyridine to optically active hydroxyethylpyridine hardly reacts with the bicyclic acetylpyridine derivative, namely 5-acetylfuro[2,3-c]pyridine.

EXAMPLE 3

Synthesis of 5-(1-(R)-hydroxyethyl)furo[2,3-c]pyridine from 5-acetylfuro[2,3-c]pyridine using *Candida maris* IFO10003; *Candida maris* IFO 10003 was deposited in the INSTITUTE FOR FERMENTATION, OSAKA (IFO)

A liquid broth (45 ml) comprising 3 g of yeast extract, 6.5 g of diammonium hydrogen phosphate, 1 g of potassium dihydrogen-phosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride, per 900 milliliters, and one drop of Adekanol were placed in a 500-ml Sakaguchi flask and sterilized, 5 ml of a sterilized 40% aqueous solution of glucose was added, and the whole was aseptically inoculated with 1 ml of the culture of *Candida maris* IFO 10003 as obtained by the culture method described in Example 1, and shake culture was carried out at 30° C. for 24 hours. The resulting culture was used as a seed yeast. A 5-liter jar fermenter was charged with 2.25 liters of the liquid broth having the above composition and 5 drops of Adekanol and, after sterilization, 250 ml of a sterilized 40% aqueous solution of glucose was added, and the whole was aseptically inoculated with 50 ml of the seed. Cultivation was carried out under the following conditions for 40 hours: cultivation temperature 30° C., rate of stirring 350 rpm, aeration 0.75 L/min. When, during cultivation, the pH was found to have become lower than 5.5, the pH was adjusted to 5.5 by adding 5 N aqueous sodium hydroxide. After cultivation, 2 L of the culture containing microbial cells, 10 g of 5-acetylfuro[2,3-c]pyridine and 60 g of glucose were placed in a 5-liter jar fermenter, and the reduction reaction was carried out at 30° C. with stirring for 22.5 hours. During the reaction, the pH of the reaction mixture was maintained at pH 6 using 5 N aqueous sodium hydroxide. At 4.5 hours and 7.5 hours after the start of the reaction, 60 g of glucose and 80 g of glucose were added, respectively. After completion of the reaction, the reaction mixture was extracted with 1 liter of ethyl acetate and the aqueous phase was further extracted with 1 liter of ethyl acetate. The organic phases were combined and dehydrated over anhydrous sodium sulfate, and the solvent was then distilled off under reduced pressure. To the residue were added 30 ml of ethyl acetate and 500 mg of active carbon, and the mixture was stirred at room temperature for 2 hours. The active carbon was removed by filtration and the solvent was then distilled off under reduced pressure. The residue was crystallized from a mixed solution composed of ethyl acetate and methylcyclohexane to give 8.1 g of 5-(1-(R)-hydroxyethyl)furo[2,3-c]pyridine as white solid. Yield: 81%, optical purity: 98.7% e.e., melting point: 59.5 to 60.5° C., specific rotation $[\alpha]_D^{20}=+37.0°$ (CHCl$_3$, c=0.56). $^1$H-NMR δ (CDCl$_3$): 1.56 (3H, d, J=6.35 Hz), 4.12 (1H, s), 5.00 (1H, q, J=6.35 Hz), 6.80 (1H, d, J=1.95 Hz), 7.54 (1H, s), 7.77 (1H, d, J=1.95 Hz), 8.80 (1H, s).

EXAMPLE 4

Synthesis of 5-(1-(S)-hydroxyethyl)furo[2,3-c]pyridine from 5-acetylfuro[2,3-c]pyridine Using *Candida tropicalis* IFO 0006

A liquid broth (225 ml) comprising 3 g of yeast extract, 6.5 g of diammonium hydrogen phosphate, 1 g of potassium dihydrogen-phosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride, per 900 milliliters, and two drops of Adekanol were placed in a 2-liter Sakaguchi flask and sterilized, 25 ml of a sterilized 40% aqueous solution of glucose was added, and the whole was aseptically inoculated with 2.5 ml of the culture of *Candida tropicalis* IFO 0006 as obtained by the culture method described in Example 1, and shake culture was carried out at 30° C. for 24 hours. After cultivation, 300 ml of the culture was centrifuged, and the cells collected were suspended in 100 ml of 100 mM phosphate buffer (pH 6.5). The cell suspension, 1 g of 5-acetylfuro[2,3-c]pyridine and 3 g of glucose were placed in a 500-ml Sakaguchi flask, and the reaction was carried out at 30° C. with stirring for 5 hours. During the reaction, the pH of the reaction mixture was maintained at pH 6.5 using 5 N aqueous sodium hydroxide. After completion of the reaction, the reaction mixture was extracted with ethyl acetate and the aqueous phase was further extracted with ethyl acetate. The organic phases were combined and dehydrated over anhydrous sodium sulfate, and the solvent was then distilled off under reduced pressure. The residue was dissolved in toluene at room temperature and the solution was cooled in ice water to cause crystallization, whereby 750 mg of 5-(1-(S)-hydroxyethyl)furo[2,3-c]pyridine was obtained as white solid. Yield 75%, optical purity 100% e.e.

EXAMPLE 5

Preparation of a Cell-Free Extract from *Candida intermedia* IFO 0761 and Synthesis of 5-(1-(S)-hydroxyethyl)furo[2,3-c]pyridine from 5-acetylfuro[2,3-c]pyridine Using the Same

*Candida intermedia* IFO 0761 was cultured by the same method of cultivation as described in Example 3 except that the 5-liter jar fermenter cultivation conditions were modified as follows: rate of stirring 700 rpm, aeration 1.5 liters/min, cultivation time 16 hours. After cultivation, 940 ml of the culture obtained was centrifuged, the cells collected were washed twice with 400-ml portions of 100 mM phosphate buffer (pH 6.5), the wet cells were suspended in 200 ml of 100 mM phosphate buffer (pH 6.5) supplemented with β-mercaptoethanol to a concentration of 5 mM, and the cells were disrupted using a Bead-Beater (product of BioSpec Products). The cell debris was removed by centrifugation, ammonium sulfate was added to 80% saturation, and the supernatant was removed by centrifugation. The sediment obtained was suspended in 15 ml of 100 mM phosphate buffer (pH 6.5) supplemented with β-mercaptoethanol to 5 mM and the suspension was dialyzed overnight against 100 mM phosphate buffer (pH 6.5) supplemented with β-mercaptoethanol to 1 mM to give 64.5 ml of a cell-free extract. The cell-free extract (0.75 ml) was added to a test tube containing 15 mg of 5-acetylfuro[2,3-c]pyridine and 104.3 mg of NADH, and the reaction was allowed to proceed at 30° C. for 4 hours. After completion of the reaction, the conversion to the product and the optical purity of the product were determined in the same manner as in Example 1. The conversion was 60.7% and the optical purity was (S) 99.5% e.e.

EXAMPLE 6

Synthesis of 5-(1-(S)-hydroxyethyl)furo[2,3-c]pyridine from 5-acetylfuro[2,3-c]pyridine Using a Cell-Free Extract from *Candida intermedia* IFO 0761

The cell-free extract (0.75 ml) from *Candida intermedia* IFO 0761 as obtained in Example 5 was added to a test tube containing 15 mg of 5-acetylfuro[2,3-c]pyridine and 126.4 mg of NADPH, and the reaction was allowed to proceed at 30° C. for 4 hours. After completion of the reaction, the conversion to the product and the optical purity of the product were determined in the same manner as in Example 1. The conversion was 51.1% and the optical purity was (S) 99.4% e.e.

EXAMPLE 7

Preparation of Acetone-Dried Cells from *Candida maris* IFO 10003 and Synthesis of 5-(1-(R)-hydroxyethyl)furo[2,3-c]pyridine from 5-acetylfuro[2,3-c]pyridine Using the Same A liquid broth (45 ml) comprising 3 g of yeast extract, 6.5 g of diammonium hydrogen phosphate, 1 g of potassium dihydrogen-phosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride, per 900 milliliters, and one drop of Adekanol were placed in a 500-ml Sakaguchi flask and sterilized, 5 ml of a sterilized 40% aqueous solution of glucose was added, and the whole was aseptically inoculated with 1 ml of the culture of *Candida maris* IFO 10003 as obtained by the culture method described in Example 1, and shake culture was carried out at 30° C. for 48 hours. After cultivation, 40 ml of the culture was centrifuged, and the cells collected were washed twice with deionized water and suspended in 40 ml of deionized water. Acetone (1.2 L) was added thereto with ice cooling and stirring, and the mixture was stirred on ice for 30 minutes. After filtration, the cells on the filter paper were washed with cooled acetone and then dried under reduced pressure to give 1.3 g of acetone-dried cells. The acetone-dried cells (10 mg), 5 mg of 5-acetylfuro[2,3-c]pyridine, 0.275 mg of $NAD^+$, 0.275 mg of $NADP^+$, 5.5 mg of glucose, 30 U of glucose dehydrogenase (GLUCDH "Amano" II, trademark, product of Amano Pharmaceutical) and 0.5 ml of 100 mM phosphate buffer were added to a test tube, and the reduction reaction was carried out at 30° C. for 24 hours. After completion of the reaction, the conversion to the product and the optical purity of the product were determined in the same manner as in Example 1. The conversion was 90.8% and the optical purity was (R) 99.9% e.e.

EXAMPLE 8

Preparation of a Cell-Free Extract from *Candida maris* IFO 10003 and Synthesis of 5-(1-(R)-hydroxyethyl)furo[2,3-c]pyridine from 5-acetylfuro[2,3-c]pyridine Using the Same

*Candida maris* IFO 10003 was cultivated by the same method of cultivation as described in Example 3 except that the 5-liter jar fermenter cultivation conditions were modified as follows: rate of stirring: 300 rpm, aeration: 0.75 L/min, cultivation time: 76 hours. Cells were centrifugally collected from 2,150 ml of the culture obtained and washed with 500 ml of 100 mM phosphate buffer (pH 6.5), and the wet cells were suspended in 430 ml of 100 mM phosphate buffer (pH 6.5) supplemented with β-mercaptoethanol to a concentration of 5 mM, and the cells were disrupted using a Bead-Beater (product of BioSpec Products). The cell debris was removed by centrifugation, and the supernatant was dialyzed overnight against 100 mM phosphate buffer (pH 6.5) supplemented with β-mercaptoethanol to 5 mM to give 289 ml of a cell-free extract. The cell-free extract (24 ml) was added to a three-necked flask containing 0.25 g of 5-acetylfuro[2,3-c]pyridine, 30 mg of $NAD^+$, 2.5 g of glucose and 300 U of glucose dehydrogenase (GLUCDH "Amano" II, trademark, product of Amano Pharmaceutical), and the reduction reaction was carried out. The reaction was allowed to proceed at 30° C. with stirring while adjusting the pH of the reaction mixture to 6.5 using 5 N aqueous sodium hydroxide. Portions of the reaction mixture were analyzed at intervals by HPLC and, each time when the substrate was found exhausted, 0.25 g of the substrate was added, and the reaction was allowed to proceed continuedly. While repeating this procedure, the reaction broth was carried out for about 72 hours. Then, the yield of 5-(1-hydroxyethyl)furo[2,3-c]pyridine was 2.2 g. The yield was 88% and the optical purity was (R) 100% e.e.

EXAMPLE 9

Synthesis of 5-(1-(R)-hydroxyethyl)furo[2,3-c]pyridine from 5-acetylfuro[2,3-c]pyridine Using a Cell-Free Extract from *Candida maris* IFO 10003)

To a three-necked flask containing 20 ml of the cell-free extract obtained in Example 8 were added 0.25 g of 5-acetylfuro [2,3-c]pyridine, 40 mg of $NAD^{30}$, 0.25 g of sodium formate and 120 U of formate dehydrogenase (product of Fluka), and the reduction reaction was carried out. The reaction was conducted at 30° C. with stirring while adjusting the pH of the reaction mixture to 6.5 with 5 N formic acid. Portions of the reaction mixture was analyzed at intervals by HPLC and, each time when the substrate was found exhausted, 0.25 g of the substrate was added, and the reaction was allowed to proceed continuedly. While repeating this procedure, the reaction was carried out for about 93 hours. After completion of the reaction, the yield of 5-(1-hydroxyethyl)furo[2,3-c]pyridine was 1.8 g. Yield: 72%, optical purity: (R) 100% e.e.

EXAMPLE 10

Synthesis of 5-(1-(R)-hydroxyethyl)furo[2,3-c]pyridine from 5-acetylfuro[2,3-c]pyridine Using Acetone-Dried Cells of *Candida maris* IFO 10003

The acetone-dried cells (20 mg) of *Candida maris* IFO 10003 as obtained in Example 7, 25 mg of 5-acetylfuro[2,3-c]pyridine, 2.2 mg of. $NAD^+$, 0.4 ml of 100 mM phosphate buffer (pH 6.5) and 0.1 ml of isopropanol were added to a test tube and the reduction reaction was carried out at 30° C. for 39.5 hours. After completion of the reaction, the conversion to the product and the optical purity of the product were determined by the same analytical methods as in Example 1. The conversion was 47.2% and the optical purity was (R) 100% e.e.

EXAMPLE 11

Synthesis of 5-(1-(R)-hydroxyethyl)furo[2,3-c]pyridine from 5-acetylfuro[2,3-c]pyridine Using a Cell-Free Extract from *Candida maris* IFO 10003

The cell-free extract (0.4 ml) from *Candida maris* IFO 10003 as obtained in Example 8, 25 mg of 5-acetylfuro[2,3-c]pyridine, 2.2 mg of $NAD^+$ and 0.1 ml of isopropanol were added to a test tube, and the reduction reaction was carried out at 30° C. for 39.5 hours. After completion of the reaction, the conversion to the product and the optical purity of the product were determined by the same analytical methods as in Example 1. The conversion was 51.8% and the optical purity was (R) 100% e.e.

REFERENCE EXAMPLE 1

Synthesis of 5-acetyl-7-chlorofuro[2,3-c]pyridine from 7-chloro-5-(1-hydroxyethyl)furo[2,3-c]pyridine 7-Chloro-5-(1-hydroxyethyl)furo[2,3-c]pyridine (1.0 g) obtained by the method described in J. Org. Chem., 63, 7851 (1998) was dissolved in 4.0 ml of methylene chloride. Thereto were added 3 ml of a saturated aqueous solution of sodium bicarbonate, 0.62 ml of a 1 M aqueous solution of sodium bromide and 0.62 ml of a 1 M solution of 2,2,6,6-tetramethyl-1-piperidinyloxy radical in methylene chloride, and the resulting mixture was vigorously stirred on ice. Thereto was added portionwise 5.74 ml of an aqueous solution of sodium hypochlorite saturated with sodium bicarbonate in advance, and the mixture was stirred on ice for 30 minutes. After completion of the reaction, ethyl acetate was added, and 10 ml of 10% aqueous sodium hydrogen sulfite was added with stirring. After phase separation, the organic phase was taken, washed with a saturated solution of sodium chloride, and dried over anhydrous sodium sulfate. The solvent was distilled off under reduced pressure and the residue was crystallized from toluene-methylcyclohexane to give 0.43 g of 5-acetyl-7-chlorofuro[2,3-c]pyridine. $^1$H-NMR δ (CDCl$_3$): 2.77 (3H, s), 7.00 (1H, d, J=1.95 Hz), 7.89 (1H, d, J=1.96 Hz), 8.32 (1H, s)

EXAMPLE 12

Asymmetric Reduction of 5-acetyl-7-chlorofuro[2,3-c]pyridine Using Various Microorganisms A liquid broth (pH 7) comprising 40 g of glucose, 3 g of yeast extract, 6.5 g of diammonium hydrogen phosphate, 1 g of potassium dihydrogen-phosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride, per liter, was distributed in 5-ml portions into large size test tubes and steam-sterilized at 120° C. for 20 minutes. These liquid broth portions were each aseptically inoculated with one loopful of one of the microorganisms listed in Table 5, and shake culture was carried out at 30° C. for 24 to 72 hours. Then, 0.5 ml of each culture was centrifuged and the cells collected were suspended in 0.5 ml of 100 mM phosphate buffer (pH 6.5) containing 8% of glucose. This cell suspension was added to a test tube containing 5 mg of 5-acetyl-7-chlorofuro[2,3-c]pyridine obtained in Reference Example 1 placed therein in advance, and the reaction was allowed to proceed at 30° C. for 26 hours. After reaction, 5 ml of ethyl acetate was added to each reaction mixture, followed by mixing up. A portion of this was analyzed under the following HPLC conditions.

[HPLC Analysis Conditions]

Column: Chiralpak AS, product of Daicel Chemical Industries; eluent: hexane/ethanol/diethylamine =92/8/0.1; flow rate: 1 ml/min; detection: 254 nm; column temperature: room temperature; elution time: 5-acetyl-7-chlorofuro[2,3-c]pyridine 7.6 minutes, 5-(1-(R)-hydroxyethyl)-7-chlorofuro[2,3-c]pyridine 10.3 minutes, 5-(1-(S)-hydroxyethyl)-7-chlorofuro[2,3-c]pyridine 15.7 minutes.

The yield, optical purity and absolute configuration of the product 5-(1-hydroxyethyl)-7-chlorofuro[2,3-c]pyridine per reaction mixture are shown in Table 5.

TABLE 5

| Microorganism | Yield (mg/ml) | Optical purity (% e.e.) | Absolute configuration |
|---|---|---|---|
| *Candida maltosa* CBS 5612 | 2.33 | 97.4 | S |
| *Candida parapsilosis* IFO 0585 | 0.32 | 70.3 | S |
| *Cryptococcus albidus* var. *albidus* IFO 0378 | 0.62 | 96.5 | S |
| *Dipodascus ovetensis* IFO 1201 | 2.07 | 97.2 | S |
| *Geotrichum candidum* CBS 178.71 | 3.35 | 98.2 | S |
| *Hyphopichia burtonii* IFO 0844 | 1.61 | 81.4 | S |
| *Lodderomyces elongisporus* IFO 1676 | 1.45 | 95.8 | S |
| *Rhodosporidium toruloides* IFO 0559 | 1.90 | 98.7 | S |
| *Sporidiobolus johnsonii* IFO 6903 | 4.24 | 98.3 | S |
| *Candida maris* IFO 10003 | 5.10 | 90.5 | R |
| *Ogataea wickerhamii* IFO 1706 | 5.85 | 18.0 | R |
| *Yamadazyma farinosa* IFO 0534 | 0.46 | 78.8 | R |

EXAMPLE 13

Asymmetric Reduction of 5-acetyl-7-chlorofuro[2,3-c]pyridine Using Various Microorganisms A liquid broth (pH 7) comprising 10 g meat extract, 10 g peptone, 5 g of yeast extract and 3 g sodium chloride, per liter, was distributed in 5-ml portions into large size test tubes and steam-sterilized at 120° C. for 20 minutes. These liquid broth portions were each aseptically inoculated with one loopful of one of the microorganisms listed in Table 6, and shake culture was carried out at 30° C. for 24 to 72 hours. Then, 2 ml of each culture was centrifuged and the cells collected were suspended in 0.5 ml of 100 mM phosphate buffer (pH 6.5) containing 8% of glucose. This cell suspension was added to a test tube containing 2.5 mg of 5-acetyl-7-chlorofuro[2,3-c]pyridine obtained in Reference Example 1 placed therein in advance, and the reaction was allowed to proceed at 30° C. for 26 hours. After reaction, the reaction mixture was analyzed in the same manner as in Example 12. The yield, optical purity and absolute configuration of the product 5-(1-hydroxyethyl)-7-chlorofuro[2,3-c]pyridine per reaction mixture are shown in Table 6.

TABLE 6

| Microorganism | Yield (mg/ml) | Optical purity (% e.e.) | Absolute configuration |
| --- | --- | --- | --- |
| Jensenia canicruria IFO 13914 | 4.37 | 99.0 | S |
| Pseudomonas stutzeri IFO 13596 | 1.30 | 99.6 | S |
| Corynebacterium acetoacidophilum ATCC 21476 | 0.24 | 64.0 | R |

EXAMPLE 14

Enzyme Purification

Hereafter, the reducing activity was measured by allowing the reaction to proceed at 30° C. for 3 minutes in 3.0 ml of a reaction mixture containing 1 mM 5-acetylfuro[2,3-c]pyridine (substrate), 0.25 mM NADH, 0.3% (vol/vol) dimethyl sulfoxide and 0.05 ml of the enzyme solution in 100 mM phosphate buffer (pH 6.5) and measuring the decrease in absorbance at the wavelength 340 nm. These conditions were employed as standard reaction conditions for reducing activity measurement. The enzyme activity oxidizing 1 μmole of NADH to $NAD^+$ in one minute under these reaction conditions was defined as 1 unit.

A liquid broth (45 ml) comprising 3 g of yeast extract, 6.5 g of diammonium hydrogen phosphate, 1 g of potassium dihydrogen-phosphate, 0.8 g of magnesium sulfate heptahydrate, 60 mg of zinc sulfate heptahydrate, 90 mg of iron sulfate heptahydrate, 5 mg of copper sulfate pentahydrate, 10 mg of manganese sulfate tetrahydrate and 100 mg of sodium chloride, per 900 milliliters, and one drop of Adekanol were placed in a 500-ml Sakaguchi flask and sterilized, 5 ml of a sterilized 40% aqueous solution of glucose was added, and the whole was aseptically inoculated with 1 ml of the culture of Candida maris IFO 10003 as obtained by preculturing in the same medium, and shake culture was carried out at 30° C. for 24 hours. The culture obtained was used as a seed yeast.

A 5-liter jar fermenter was charged with 2.25 liters of the liquid broth having the above composition and 5 drops of Adekanol and, after sterilization, 250 ml of a sterilized 40% aqueous solution of glucose was added, and the whole was aseptically inoculated with 50 ml of the seed yeast. Cultivation was carried out under the following conditions for 140 hours: cultivation temperature 30° C., rate of stirring 300 rpm, aeration 0.3 L/min. When, during cultivation, the pH was found to have become lower than 5.5, the pH was adjusted to 5.5 with 5 N aqueous sodium hydroxide.

Ten liters of the culture obtained by the above cultivation method was centrifuged, the cells collected were washed twice with 5-liter portions of physiological saline, the wet cells were suspended in 1,200 ml of 100 mM Tris-hydrochloride buffer (pH 7.5) containing 5 mM β-mercaptoethanol and 0.1 mM PMSF and the cells were disrupted using a Dyno-mill (product of Dyno Mill). The cell debris was removed by centrifugation and 1,760 ml of a cell-free extract was obtained.

Protamine sulfate (3 g) was added to this cell-free extract and, after overnight stirring at 4° C., the resulting precipitate was removed by centrifugation. Ammonium sulfate was added to the supernatant to 35% saturation and, after 1 hour of stirring at 0° C., the resulting precipitate was removed by centrifugation. Ammonium sulfate was added to the supernatant to 65% saturation and, after 1 hour of stirring at 0° C., the resulting precipitate was collected by centrifugation and suspended in 200 ml of 20 mM Tris-hydrochloride buffer (pH 7.5) containing 5 mM β-mercaptoethanol, and the suspension was dialyzed against 30 L of the same buffer.

The dialyzate was applied to a DEAE-TOYOPEARL 650M (product of Tosoh) column (340 ml) equilibrated beforehand with 20 mM Tris-hydrochloride buffer (pH 7.5) containing 5 mM-mercaptoethanol to thereby allow the enzyme to be adsorbed, and the active fraction was eluted by a linear concentration gradient of sodium chloride (from 0 mM to 50 mM). Ammonium sulfate was added to this active fraction to a final concentration of 0.5 M, the resulting mixture was applied to a Phenyl-TOYOPEARL 650 M (product of Tosoh) column (74 ml) equilibrated in advance with 20 mM Tris-hydrochloride buffer (pH 8.5) containing 5 mM β-mercaptoethanol and 0.5 M ammonium sulfate to thereby cause enzyme adsorption, the column was washed with the same buffer and the active fraction was eluted by a liner concentration gradient of ammonium sulfate (from 0.5 M to 0 M). The active eluate fractions were combined and an electrophoretically single purified enzyme specimen was thus obtained. The molecular weight of the band in SDS-PAGE was about 29,000. Upon gel filtration analysis using a TSK-G 3000 SW (product of Tosoh) column (7.8 mm I.D.×30 cm) and 0.1 M phosphate buffer (pH 7.0) containing 0.1 M sodium sulfate as the eluent, the molecular weight was about 60,000. Hereinafter, this enzyme is referred to as FPDH.

EXAMPLE 15

Optimal Temperature for the Activity of FPDH

Activity measurements were conducted under the standard reaction conditions for reducing activity measurement as described in Example 14 except that the temperature alone was varied from 20 to 80° C. As a result, the optimal temperature was found to be 50 to 55° C.

EXAMPLE 16

Optimal pH for the Activity of FPDH

Activity measurements were conducted under the standard reaction conditions for reducing activity measurement as described in Example 14 while varying the pH within the range of 3.5 to 9.0 using acetate buffer, phosphate buffer and Tris-hydrochloride buffer as the buffer solution. As a result, the optimal pH was found to be 5.0-6.0.

EXAMPLE 17

Behaviors of FPDH Against Inhibitors

Activity measurements were conducted under the standard reaction conditions for reducing activity measurement as described in Example 14 adding various compounds and metal salts as possible inhibitors at the respective concentrations shown in Table 7. The results are shown in Table 7 in terms of relative activity with the activity obtained without inhibitor addition being taken as 100%. As a result, the enzyme activity was inhibited by the mercury ion.

TABLE 7

| Inhibitor | Conc. (mM) | Relative activity (%) |
|---|---|---|
| DTNB | 0.01 | 98 |
| Iodoacetic acid | 1.0 | 80 |
| Dithiothreitol | 1.0 | 93 |
| 2-Mercaptoethanol | 1.0 | 94 |
| N-ethylmaleimide | 1.0 | 84 |
| p-Chloromercuribenzoic acid | 0.1 | 100 |
| EDTA | 1.0 | 98 |
| 1,10-Phenanthroline | 1.0 | 98 |
| Quercetin | 0.01 | 78 |
| Diphenylhydantoin | 0.5 | 102 |
| $MgSO_4$ | 1.0 | 81 |
| $MnCl_2$ | 1.0 | 76 |
| $ZnSO_4$ | 1.0 | 74 |
| $CuSO_4$ | 1.0 | 103 |
| $CoCl_2$ | 1.0 | 85 |
| $HgCl_2$ | 1.0 | 0 |

EXAMPLE 18

Specificity of FPDH

The reducing activity of FPDH was examined against various compounds. Activity measurements were conducted under the standard reaction conditions for reducing activity measurement using various carbonyl compounds shown in Table 8 and Table 9 as substrates in lieu of 5-acetylfuro[2,3-c]pyridine. In Table 8 and Table 9, the results are shown in terms of relative activity with the reducing activity when 5-acetylfuro[2,3-c]pyridine was used as the substrate being taken as 100%. As a result, FPDH had reducing activity against ketones and aldehydes but the reducing activity thereof was very low against carbocyclic ketones and the ketone in position α to a carboxyl group.

TABLE 8

| Substrate (1 mM) | Relative activity (%) |
|---|---|
| 5-Acetylfuro[2,3-c]pyridine | 100 |
| 1-Chloro-5-acetylfuro[2,3-c]pyridine | 66 |
| 2-Acetylpyridine | 111 |
| 3-Acetylpyridine | 107 |
| 4-Acetylpyridine | 130 |
| Acetylpyrazine | 133 |
| 2-Acetylpyrrole | 100 |
| 2-Acetylthiophene | 77 |
| 2-Acetylfuran | 43 |
| 2-Acetylthiazole | 86 |
| Acetophenone | 88 |
| m-Nitroacetophenone | 136 |
| p-Nitroacetophenone | 116 |
| o-Chloroacetophenone | 9 |
| m-Chloroacetophenone | 120 |
| p-Chloroacetophenone | 88 |
| p-Fluoroacetophenone | 88 |
| 2-Hydroxyacetophenone | 54 |
| 2,3'-Dichloroacetophenone | 19 |
| Benzylacetone | 96 |
| Acetone | 40 |
| 2-Butanone | 94 |
| 2-Pentanone | 67 |
| 2-Hexanone | 38 |
| 2-Octanone | 38 |
| Methyl isopropyl ketone | 43 |
| Methyl isobutyl ketone | 14 |
| Acetoin | 43 |
| Diacetyl | 107 |
| Acetylacetone | 123 |

TABLE 8-continued

| Substrate (1 mM) | Relative activity (%) |
|---|---|
| Diethyl ketone | 22 |
| Chloroacetone | 99 |
| 1-Acetylcyclopentanone | 86 |
| 1-Acetylcyclohexanone | 68 |
| Methyl pyruvate | 132 |
| Ethyl pyruvate | 133 |

TABLE 9

| Substrate (1 mM) | Relative activity (%) |
|---|---|
| Methyl acetoacetate | 128 |
| Ethyl acetoacetate | 141 |
| Ethyl 2-chloroacetoacetate | 88 |
| Pyruvic acid | 3 |
| 2-Ketobutyric acid | 5 |
| 2-Keto-n-valeric acid | 7 |
| Oxalacetic acid | 4 |
| Cyclopentanone | 3 |
| Cycloheptanone | 4 |
| 1-Tetralone | 2 |
| 2-Tetralone | 0 |
| Camphorquinone | 3 |
| Cyclohexanone | 4 |
| Pyridine-2-aldehyde | 54 |
| Pyridine-3-aldehyde | 47 |
| Pyridine-4-aldehyde | 64 |
| Benzaldehyde | 94 |
| o-Nitrobenzaldehyde | 9 |
| m-Nitrobenzaldehyde | 103 |
| p-Nitrobenzaldehyde | 162 |
| o-Chlorobenzaldehyde | 0 |
| m-Chlorobenzaldehyde | 111 |
| p-Chlorobenzaldehyde | 104 |
| Acetaldehyde | 36 |
| Propionaldehyde | 70 |
| n-Butyr aldehyde | 123 |
| n-Hexyl aldehyde | 71 |

Further, FPDH was examined for oxidation activity against various compounds. The oxidation activity was measured by allowing the reaction to proceed at 30° C. for 3 minutes in 3.0 ml of a reaction mixture containing 1 mM substrate, 0.25 mM $NAD^+$, 0.3% (vol/vol) dimethyl sulfoxide and 0.05 ml of the enzyme solution in 100 mM phosphate buffer (pH 8.0) and measuring the increase in absorbance at the wavelength 340 nm. These conditions were employed as standard reaction conditions for oxidizing activity substrate measurement. The enzyme activity reducing 1 μmole of $NAD^+$ to NADH in one minute under these reaction conditions was defined as 1 unit. The data shown in Table 10 are relative activities with the oxidation activity against the substrate 5-(1-(R)-hydroxyethyl)furo[2,3-c]pyridine being taken as 100%. As a result, it was found that FPDH has oxidation activity against various compounds.

TABLE 10

| Substrate (1 mM) | Relative activity (%) |
|---|---|
| (R)-5-(1-Hydroxyethyl)furo[2,3-c]pyridine | 100 |
| 1-(2-Pyridyl)ethanol | 23 |
| 1-(3-Pyridyl)ethanol | 110 |
| 1-(4-Pyridyl)ethanol | 24 |
| Isopropanol | 226 |
| 1-Buten-3-ol | 261 |

TABLE 10-continued

| Substrate (1 mM) | Relative activity (%) |
| --- | --- |
| 4-Penten-2-ol | 172 |
| 4-Phenyl-2-butanol | 219 |
| (R)-1-Phenylethanol | 225 |

EXAMPLE 19

Synthesis of 5-(1-(R)-hydroxyethyl)furo[2,3-c]pyridine from 5-acetylfuro[2,3-c]pyridine Using FPDH Stirred was 0.5 ml of 0.1 M phosphate buffer (pH 6.5) containing 0.5 unit of FPDH obtained in Example 14, 5 mg of 5-acetylfuro[2,3-c]pyridine, 20 mg of glucose, 0.5 mg of NAD+ and 4 units of glucose dehydrogenase (product of Amano Pharmaceutical) at 30° C. for 17 hours. After reaction, the reaction mixture was analyzed in the same manner as in Example 1. As a result, the formation of 5-(1-(R)-hydroxyethyl)furo[2,3-c]pyridine with an optical purity of 100% e.e. with 100% conversion was confirmed.

EXAMPLE 20

Synthesis of 7-chloro-5-(1-(R)-hydroxyethyl)furo[2,3-c]pyridine from 5-acetyl-7-chlorofuro[2,3-c]pyridine Using FPDH Stirred was 0.5 ml of 0.1 M phosphate buffer (pH 6.5) containing 0.5 unit of FPDH obtained in Example 14, 5 mg of 5-acetyl-7-chlorofuro[2,3-c]pyridine, 20 mg of glucose, 0.5 mg of NAD+ and 4 units of glucose dehydrogenase (product of Amano Pharmaceutical) at 30° C. for 3 hours. After reaction, the reaction mixture was analyzed in the same manner as in Example 12. As a result, the formation of 7-chloro-5-(1-(R)-hydroxyethyl)furo[2,3-c]pyridine with an optical purity of >99% e.e. with 66.9% of conversion was confirmed.

EXAMPLE 21

FPDH Gene Cloning (Chromosomal DNA Preparation)

Chromosomal DNA was extracted from a culture of *Candida maris* IFO 10003 by the method described by Hereford (Cell, 18, 1261 (1979)).

(FDPH Gene Cloning by PCR)

Purified FPDH obtained as described in Example 14 was denatured in the presence of 8 M urea and then digested with Aebromobacter-derived lysyl endopeptidase (product of Wako Pure Chemical Industries) and the peptide fragments obtained were sequenced by the Edman method. Considering the DNA sequences deduced from the amino acid sequences, two PCR primers were synthesized (primer 1: 5'-GGNGCNATHGTNAAYATGGG-3'(SEQ ID NO.: 3), primer 2: 5'-CCDATNGGRTGYTGNGTDAT-3'(SEQ ID NO.: 4).

A buffer solution (100 µl) for ExTaq containing the two primers (primer 1 and primer 2, 100 picomoles each), 660 ng of the chromosomal DNA, 20 nanomoles of each dNTP and 2.5 U of ExTaq (product of Takara Shuzo) was prepared, and 40 cycles of thermal denaturation (95° C., 1 min), annealing (40° C., 1 min) and elongation reaction (65° C., 2 min) were conducted and, after cooling to 4° C., an amplified DNA was confirmed by agarose gel electrophoresis.

(Subcloning of the PCR-Amplified DNA)

The amplified DNA was subcloned into the pT7Blue vector (product of Novagen) and the base sequence thereof was determined. As a result, the amplified DNA was found to be comprised of 230 bases including the primer sequences. The sequence is the DNA sequence portion doubly underlined in the DNA sequence shown in FIG. 1. Hereinafter, this sequence is referred to as "core sequence".

(Cloning of Sequences Adjacent to the Core Sequence by Inverse PCR)

Based on the complementary sequence GGAGCGGCCA-CATACGAGTGAATGG (primer 3(SEQ ID NO.: 5) of a portion close to the 5' side of the core sequence and the sequence AGACACCATTGCTTGATATTTGCCC (primer 4 (SEQ ID NO.: 6) of a portion close to the 3' side, two PCR primers (primer 3(SEQ ID NO.: 5') and primer 4(SEQ ID NO.: 6) identical in sequence to those sequences were synthesized.

For preparing a template for inverse PCR, the chromosomal DNA of *Candida maris* IFO 10003 was first digested with the restriction enzyme PstI and the digest was self-circularized using T4 DNA ligase. A buffer solution (100.mu.1) for ExTaq containing 660 ng of the self-circularization product, the two primers (primer 3, (SEQ ID NO.: 5) and primer 4, (SEQ ID NO.: 56, 100 picomoles each), 20 nanomoles of each dNTP and 2.5 U of ExTaq (product of Takara Shuzo) was prepared, and 40 cycles of thermal denaturation (94° C., 0.5 mm), annealing (55° C., 0.5 min) and elongation reaction (72° C., 1 min) were conducted and, after cooling to 4° C., an amplified DNA was confirmed by agarose gel electrophoresis.

The amplified DNA was subcloned into the pT7Blue vector (product of Novagen) and the base sequence thereof was determined. Based on this result and the core sequence data, the whole base sequence of the DNA coding for FPDH was determined. That whole base sequence and the deduced amino acid sequence encoded by said DNA are shown in FIG. 1. In FIG. 1, the singly underlined portions indicate those amino acid sequences which could have been determined by the Edman method with the peptide fragments formed upon digestion of purified FPDH with lysyl endopeptidase. The amino acid sequence of FPDH derived from *Candida maris* IFO 10003 is shown under SEQ ID NO:1 in the sequence listing. The base sequence of the DNA coding for that FPDH is shown under SEQ ID NO:2 in the sequence listing.

EXAMPLE 22

Construction of a Recombinant Vector Containing the FPDH Gene

For causing FPDH expression in Escherichia coli, a recombinant vector to be used for transformation was constructed. First, a double-stranded DNA was prepared which had an NdeI site added to the initiation codon site of the structural gene for FPDH and a new termination codon and an EcoRI site added immediately behind the termination codon, in the following manner. Based on the base sequence determined in Example 21, a primer 5 (5'-CGCCATATGTC-CTACAATTTTGCCAAC-3'(SEQ ID NO.: 7) with an NdeI site added to the initiation codon portion of the structural gene for FPDH and a primer 6 (5'-GCGGAATTCTTAT-TATCTTGCGGTATAACCACC-3'(SEQ ID NO.: 8)) with a new termination codon and an EcoRi site added immediately behind the termination codon of the structural gene for FPDH were synthesized.

A buffer solution (100 μl) for ExTaq containing the two primers (primer 5 and primer 6, 100 picomoles each), 132 ng of the *Candida maris* IFO 10003-derived chromosomal DNA, 20 nanomoles of each dNTP and 2.5 U of ExTaq (product of Takara Shuzo) was prepared, and 30 cycles of thermal denaturation (94° C., 0.5 min), annealing (60° C., 0.5 min) and elongation reaction (72° C., 1 min) were conducted and, after cooling to 4° C., an amplified DNA was confirmed by agarose gel electrophoresis. This amplified fragment was digested with NdeI and EcoRI and the digest was inserted into the plasmid pUCNT (WO 94/03613) at the NdeI-EcoRI site downstream from the lac promoter, whereby a recombinant vector, pNTFP, was obtained. The construction scheme for and the structure of pNTFP are shown in FIG. 2.

EXAMPLE 23

Construction of a Recombinant Vector Containing Both the FPDH Gene and the Glucose Dehydrogenase Gene A double-stranded DNA comprising the Bacillus megaterium IAM 1030-derived glucose dehydrogenase (hereinafter referred to as GDH) gene with the Escherichia coli Shine-Dalgarno sequence (9 nucleotides) added at 5 bases upstream of the initiation codon of that gene and, further, with an EcoRI digested site added just before that sequence and an SalI digested site added just behind the termination codon was prepared in the following manner. Based on the information on the base sequence of the GDH gene, a primer 7 (5'-GCCGAATTCTAAGGAGGTTAACAATG-TATAAAGATTTAGAAGG-3'(SEp ID NO.: 9) with the Escherichia coli Shine-Dalgarno sequence (9 nucleotides) added at 5 bases upstream of the initiation codon of the GDH structural gene and, further, with an EcoRI digested site added just before that sequence, and a primer 8 (5'-GCG-GTCGACTTATCCGCGTCCTGCTTGG-3'(SEO ID NO.: 10) with an SalI site added just behind the termination codon of the GDH structural gene were synthesized in the conventional manner. Using these two primers, a double-stranded DNA was synthesized by PCR using the plasmid pGDK1 (Eur. J. Biochem., 186, 389 (1989)) as the template. The DNA fragment obtained was digested with EcoRI and SalI, and the digested fragment was inserted into pNTFP constructed in Example 22 at the EcoRi-SalI site thereof to give a recombinant vector, pNTFPG. The construction scheme for and the structure of pNTFPG are shown in FIG. 2.

EXAMPLE 24

Constraction of Recombinant *Escherichia coli*

*Escherichia coli* HB101 (product of Takara Shuzo) was transformed with the recombinant vector pNTFP obtained in Example 22 and the recombinant vector pNTFPG obtained in Example 23 to give recombinant *Escherichia coli* HB101 (pNTFP) and HB101 (pNTFPG), respectively. The thus-obtained transformants, namely *Escherichia coli* HB101 (pNTFP) and *Escherichia coli* HB101 (pNTFPG), have been deposited with the Ministry of International Trade and Industry National Institute of Bioscience and Human Technology (address: 1-3 Higashi-1-chome, Tsukuba City, Ibaraki Prefecture, Japan) under the accession numbers FERM BP-7116 (deposited Apr. 11, 2000) and FERM BP-7117 (deposited Apr. 11, 2000), respectively.

Further, a recombinant vector, pSTVG, was constructed by inserting a DNA fragment of about 0.9 kb obtained by double digestion of the plasmid pGDA2 (J. Biol. Chem., 264, 6381 (1989)) with EcoRI and PstI and containing the *Bacillus megaterium*-derived GDH gene into the plasmid pSTV28 (product of Takara Shuzo) at the EcoRI-PstI site thereof. *Escherichia coli* HB101 (pNTFP) rendered competent in advance by the calcium chloride method was transformed with that pSTVG with a high introduction percentage, whereby *Escherichia coli* HB101 (pNTFP, pSTVG) was readily obtained.

EXAMPLE 25

Expression of FPDH in Recombinant *Escherichia coli*

The recombinant *Escherichia coli* HB101 (pNTFP) obtained in Example 24 was cultured on 2×YT medium (1.6% (w/v) Bacto Tryptone, 1.0% (w/v) Bacto yeast extract, 0.5% (w/v) NaCl, pH 7.0) containing 120 μg/ml of ampicillin. Cells were collected, suspended in 100 mM Tris-hydrochloride buffer (pH 7) and sonicated to give a cell-free extract. The FPDH activity of this cell-free extract was determined by the method described in Example 14. The result is shown in Table 11 in terms of specific activity.

TABLE 11

| Strain | Specific FPDH activity (U/mg) |
| --- | --- |
| HB101 (pUCNT) | <0.1 |
| HB101 (pNTFP) | 12.7 |

With *Escherichia coli* HB101 (pNTFP), a distinct increase in FPDH activity was observed as compared with the transformant obtained by using the vector plasmid alone, namely *Escherichia coli* HB101 (pUCNT).

EXAMPLE 26

Simultaneous Expression of FPDH and GDH in Recombinant *Escherichia coli*

The recombinant *Escherichia coli* HB101 (pNTFPG) obtained in Example 24 and the recombinant *Escherichia coli* HB101 (pNTFP, pSTVG) were treated in the same manner as in Example 25, and the cell-free extracts obtained were assayed for FPDH activity and GDH activity. The GDH activity was measured by adding 0.1 M glucose (substrate), 2 mM $NADP^+$ (coenzyme) and the enzyme to 1 M Tris-hydrochloride buffer (pH 8.0) and measuring the increase in absorbance at the wavelength 340 nm at 25° C. The enzyme activity capable of reducing 1 μmole of $NADP^+$ to NADPH in 1 minute under these reaction conditions was defined as 1 unit. The FPDH activity was determined in the same manner as in Example 14. The thus-measured FPDH activity and GDH activity of each cell-free extract are shown in Table 12 in terms of specific activity.

TABLE 12

| Strain | Specific FPDH activity (U/mg) | Specific GDH activity (U/mg) |
| --- | --- | --- |
| HB101 (pUCNT) | <0.1 | <0.01 |
| HB101 (pNTFP) | 12.7 | <0.01 |
| HB101 (pNTFPG) | 7.5 | 86.7 |
| HB101 (pNTFP, pSTVG) | 11.3 | 1.13 |

*Escherichia coli* HB101 (pNTFPG) and *Escherichia coli* HB101 (pNTFP, pSTVG) each showed evident increases in FPDH and GDH activities as compared with the transformant obtained by using the vector plasmid alone, namely *Escherichia coli* HB101 (pUCNT).

EXAMPLE 27

Synthesis of 5-(1-(R)-hydroxyethyl)furo[2,3-c]pyridine from 5-acetylfuro[2,3-c]pyridine Using the Recombinant *Escherichia coli* Having the FPDH Gene Introduced Therein, Under the Conditions Resulting from the Addition of Isopropanol to the Reaction System 2×YT medium (50 ml) placed in a 500-ml Sakaguchi flask and sterilized was inoculated with the recombinant *Escherichia coli* HB101 (pNTFP) obtained in Example 24, and shake culture was carried out at 37° C. for 18 hours. One milliliter of the culture obtained was adjusted to pH 7.0, 50 mg of 5-acetylfuro[2,3-c]pyridine, 150 μl of isopropanol and 0.22 mg of NAD$^+$ were added thereto, and the mixture was stirred at 30° C. for 7.5 hours. After completion of the reaction, the conversion to and the optical purity of the product 5-(1-hydroxyethyl)furo[2,3-c]pyridine were determined by the same analytical methods as used in Example 1. The conversion was 95.7% and the optical purity was (R) 100% e.e.

EXAMPLE 28

Synthesis of 5-(1-(R)-hydroxyethyl)furo[2,3-c]pyridine from 5-acetylfuro[2,3-c]pyridine Using the Recombinant *Escherichia coli* Having the FPDH Gene Introduced Therein, with GDH Separately Added to the Reaction System 2×YT medium (50 ml) placed in a 500-ml Sakaguchi flask and sterilized was inoculated with the recombinant *Escherichia coli* HB101 (pNTFP) obtained in Example 24, and shake culture was carried out at 37° C. for 18 hours. To 20 ml of the culture obtained were added 540 units of glucose dehydrogenase (product of Amano Pharmaceutical), 1.0 g of 5-acetylfuro[2,3-c]pyridine, 3 mg of NAD$^+$ and 3 g of glucose and, while adjusting the pH to 6.5 by dropwise addition of 2.5 M aqueous sodium hydroxide, the mixture was stirred at 30° C. for 29 hours. After completion of the reaction, the conversion to and the optical purity of the product 5-(1-hydroxyethyl)furo[2,3-c]pyridine were determined by the same analytical methods as used in Example 1. The conversion was 97.1% and the optical purity was (R) 100% e.e.

EXAMPLE 29

Synthesis of 5-(1-(R)-hydroxyethyl)furo[2,3-c]pyridine from 5-acetylfuro[2,3-c]pyridine Using the Recombinant *Escherichia coli* Under Simultaneous Expression of FPDH and GDH 2×YT medium (50 ml) placed in a 500-ml Sakaguchi flask and sterilized was inoculated with the recombinant *Escherichia coli* HB101 (pNTFPG) obtained in Example 24, and shake culture was carried out at 37° C. for 18 hours. To 20 ml of the culture obtained were added 1.0 g of 5-acetylfuro [2,3-c]pyridine, 3 mg of NAD$^+$ and 3 g of glucose and, while adjusting the pH to 6.5 by dropwise addition of 2.5 M aqueous sodium hydroxide, the mixture was stirred at 30° C. At 6 hour during the reaction, 1.0 g of 5-acetylfuro[2,3-c] pyridine and 3.0 g of glucose were added. After 29 hours of stirring, the yield and optical purity of the product 5-(1-hydroxyethyl)furo[2,3-c]pyridine were determined by the same analytical methods as used in Example 1. The yield was 2.66 g and the optical purity was (R) 100% e.e.

EXAMPLE 30

Synthesis of 5-(1-(R)-hydroxyethyl)furo[2,3-c]pyridine from 5-acetylfuro[2,3-c]pyridine Using the Recombinant *Escherichia coli* Under Simultaneous Expression of FPDH and GDH Under the Conditions Resulting from the Addition of Butyl Acetate to the Reaction System 2×YT medium (50 ml) placed in a 500-ml Sakaguchi flask and sterilized was inoculated with the recombinant *Escherichia coli* HB101 (pNTFPG) obtained in Example 24, and shake culture was carried out at 37° C. for 18 hours. To 20 ml of the culture obtained were added 4.0 g of 5-acetylfuro [2,3-c]pyridine, 3 mg of NAD$^+$, 6 g of glucose and 20 ml of butyl acetate and, while adjusting the pH to 6.5 by dropwise addition of 5 M aqueous sodium hydroxide, the mixture was stirred at 30° C. At 9 hour during the reaction, 1.0 g of 5-acetylfuro[2,3-c]pyridine and 1.5 g of glucose were added. After 78 hours of stirring with timely addition of NAD$^+$, the yield and optical purity of the product 5-(1-hydroxyethyl) furo[2,3-c]pyridine were determined by the same analytical methods as used in Example 1. The yield was 4.98 g and the optical purity was (R) 100% e.e.

EXAMPLE 31

Synthesis of 5-(1-(S)-hydroxyethyl)furo[2,3-c]pyridine from 5-(1-hydroxyethyl)furo[2,3-c]pyridine Using the Recombinant *Escherichia coli* Having the FPDH Gene 2×YT medium (50 ml) placed in a 500-ml Sakaguchi flask and sterilized was inoculated with the recombinant *Escherichia coli* HB101 (pNTFP) obtained in Example 24, and shake culture was carried out at 37° C. for 18 hours. One milliliter of the culture obtained was adjusted to pH 6.5, 10 mg of 5-(1-hydroxyethyl)furo[2,3-c]pyridine (optical purity 0% e.e.), 50 μl of acetone and 0.1 mg of NAD$^+$ were added thereto, and the mixture was stirred at 30° C. for 7 hours. After completion of the reaction, the yield of 5-acetylfuro [2,3-c]pyridine and the residual amount and optical purity of 5-(1-hydroxyethyl)furo[2,3-c]pyridine were determined by the same analytical methods as used in Example 1. The yield of 5-acetylfuro[2,3-c]pyridine was 4.71 mg and the residual amount of 5-(1-hydroxyethyl)furo[2,3-c]pyridine was 5.29 mg and the optical purity thereof was (S) 89.2% e.e.

EXAMPLE 32

Synthesis of 5-(1-(S)-hydroxyethyl)furo[2,3-c]pyridine from 5-(1-hydroxyethyl)furo[2,3-c]pyridine Using the Recombinant *Escherichia coli* Having the FPDH Gene 2×YT medium (50 ml) placed in a 500-ml Sakaguchi flask and sterilized was inoculated with the recombinant *Escherichia coli* HB101 (pNTFP) obtained in Example 24, and shake culture was carried out at 37° C. for 18 hours. One milliliter of the culture obtained was adjusted to pH 6.5, 10 mg of 5-(1-hydroxyethyl)furo[2,3-c]pyridine (optical purity 0% e.e.) was added thereto, and the mixture was stirred at 30° C. for 7 hours. After completion of the reaction, the yield of 5-acetylfuro[2,3-c]pyridine and the residual amount and optical purity of 5-(1-hydroxyethyl)furo[2,3-c]pyridine were determined by the same analytical methods as used in Example 1. The yield of 5-acetylfuro[2,3-c]pyridine was 4.98 mg and the residual amount of 5-(1-hydroxyethyl)furo[2,3-c]pyridine was 5.02 mg and the optical purity thereof was (S) 99.2% e.e.

INDUSTRIAL APPLICABILITY

The invention makes it possible to produce an optically active pyridineethanol derivative in high yields by stereoselectively reducing acetylpyridine derivatives by causing an enzyme or enzyme source having asymmetric reduction activity to act thereon. It also provides a novel enzyme, a DNA coding for said enzyme, a recombinant vector having said DNA, and a transformant having said recombinant vector. By using said enzyme and said transformant, it is possible to produce an optically active pyridineethanol derivative efficiently.

The invention claimed is:

1. An isolated polypeptide specified below under (a) or (b):
   (a) a polypeptide comprising the amino acid sequence of SEQ ID NO:1; or
   (b) a mutant of the polypeptide of (a), wherein said mutant consists of one amino acid deletion, substitution or addition and wherein said mutant has the activity of stereoselectively reducing 5-acetylfuro[2,3-c]pyridine to 5-(1-(R)-hydroxyethyl)furo[2,3-c]pyridine.

* * * * *

SEQUENCE LISTING

```
<160> NUMBER OF SEQ ID NOS: 2

<210> SEQ ID NO 1
<211> LENGTH: 254
<212> TYPE: PRT
<213> ORGANISM: Candida maris

<400> SEQUENCE: 1

Met Ser Tyr Asn Phe Ala Asn Lys Val Leu Ile Val Thr Gly Gly Leu
  1               5                  10                  15

Ser Gly Ile Gly Leu Ala Val Ala Lys Lys Phe Leu Gln Leu Gly Ala
             20                  25                  30

Lys Val Thr Ile Ser Asp Ile Ser Ala Thr Glu Lys Tyr Asn Thr Val
         35                  40                  45

Val Gly Glu Phe Lys Thr Glu Gly Ile Asp Val Lys Asn Val Gln Tyr
     50                  55                  60

Ile Gln Ala Asp Ala Ser Lys Glu Ala Asp Asn Glu Lys Leu Ile Ser
 65                  70                  75                  80

Glu Thr Leu Ser Ala Phe Gly Asp Leu Asp Tyr Val Cys Ala Asn Ala
                 85                  90                  95

Gly Ile Ala Thr Phe Thr Gln Thr Thr Asp Ile Ser Tyr Asp Val Trp
            100                 105                 110

Arg Lys Val Thr Ser Ile Asn Leu Asp Gly Val Phe Met Leu Asp Lys
        115                 120                 125

Leu Ala Ala Gln Tyr Phe Leu Ser Lys Asn Lys Pro Gly Ala Ile Val
    130                 135                 140

Asn Met Gly Ser Ile His Ser Tyr Val Ala Ala Pro Gly Leu Ser His
145                 150                 155                 160

Tyr Gly Ala Ala Lys Gly Gly Leu Lys Leu Leu Thr Gln Thr Met Ala
                165                 170                 175

Leu Glu Tyr Ala Ala Lys Gly Ile Arg Val Asn Ser Val Asn Pro Gly
            180                 185                 190

Tyr Ile Lys Thr Pro Leu Leu Asp Ile Cys Pro Lys Glu His Met Asp
        195                 200                 205

Tyr Leu Ile Thr Gln His Pro Ile Gly Arg Leu Gly Lys Pro Glu Glu
    210                 215                 220
```

```
Ile Ala Ser Ala Val Ala Phe Leu Cys Ser Asp Glu Ala Thr Phe Ile
225                 230                 235                 240

Asn Gly Ile Ser Leu Leu Val Asp Gly Gly Tyr Thr Ala Arg
            245                 250

<210> SEQ ID NO 2
<211> LENGTH: 765
<212> TYPE: DNA
<213> ORGANISM: Candida maris

<400> SEQUENCE: 2 atg tcc tac aat ttt gcc aac aaa gtt ctt att gtg acc gga ggt ctg      48
Met Ser Tyr Asn Phe Ala Asn Lys Val Leu Ile Val Thr Gly Gly Leu
1               5                   10                  15 tcc ggt att gga ctt gca gtt gca aag aag ttt ctt caa ctc ggg gcc      96
Ser Gly Ile Gly Leu Ala Val Ala Lys Lys Phe Leu Gln Leu Gly Ala
            20                  25                  30 aaa gtg aca att tct gat att tct gcc act gaa aag tac aac acg gtt     144
Lys Val Thr Ile Ser Asp Ile Ser Ala Thr Glu Lys Tyr Asn Thr Val
        35                  40                  45 gta ggt gag ttc aaa acc gag ggc att gat gtc aag aat gtt cag tat     192
Val Gly Glu Phe Lys Thr Glu Gly Ile Asp Val Lys Asn Val Gln Tyr
 50                  55                  60 att cag gcc gat gca agc aaa gag gcc gac aac gag aag ctc atc tcc     240
Ile Gln Ala Asp Ala Ser Lys Glu Ala Asp Asn Glu Lys Leu Ile Ser
65                  70                  75                  80 gag aca ctg tct gct ttc ggt gat ctc gac tac gtg tgc gca aat gct     288
Glu Thr Leu Ser Ala Phe Gly Asp Leu Asp Tyr Val Cys Ala Asn Ala
                85                  90                  95 gga att gcc act ttc aca cag act aca gat atc tcc tac gac gtc tgg     336
Gly Ile Ala Thr Phe Thr Gln Thr Thr Asp Ile Ser Tyr Asp Val Trp
            100                 105                 110 agg aag gta acc agc att aat ctt gac ggt gtt ttc atg ctt gat aaa     384
Arg Lys Val Thr Ser Ile Asn Leu Asp Gly Val Phe Met Leu Asp Lys
        115                 120                 125 cta gct gca caa tac ttt ttg agc aag aac aag cca ggt gct att gtc     432
Leu Ala Ala Gln Tyr Phe Leu Ser Lys Asn Lys Pro Gly Ala Ile Val
130                 135                 140 aac atg ggt tcc att cac tcg tat gtg gcc gct cct gga ctt tct cac     480
Asn Met Gly Ser Ile His Ser Tyr Val Ala Ala Pro Gly Leu Ser His
145                 150                 155                 160 tac ggt gcg gcc aaa gga ggt ctg aag cta ctg act cag acc atg gcc     528
Tyr Gly Ala Ala Lys Gly Gly Leu Lys Leu Leu Thr Gln Thr Met Ala
                165                 170                 175 ctt gag tat gcc gca aaa ggt ata aga gtt aac tcg gtc aat cct ggt     576
Leu Glu Tyr Ala Ala Lys Gly Ile Arg Val Asn Ser Val Asn Pro Gly
            180                 185                 190 tac atc aag aca cca ttg ctt gat att tgc cct aaa gaa cac atg gat     624
Tyr Ile Lys Thr Pro Leu Leu Asp Ile Cys Pro Lys Glu His Met Asp
        195                 200                 205 tac ctt atc act cag cat cca att gga cgt ctc gga aag cct gaa gag     672
Tyr Leu Ile Thr Gln His Pro Ile Gly Arg Leu Gly Lys Pro Glu Glu
210                 215                 220 att gca agt gct gtt gca ttt ctg tgc tct gac gag gct aca ttt atc     720
Ile Ala Ser Ala Val Ala Phe Leu Cys Ser Asp Glu Ala Thr Phe Ile
225                 230                 235                 240 aac gga atc tcc ttg ttg gta gac ggt ggt tat acc gca aga taa         765
Asn Gly Ile Ser Leu Leu Val Asp Gly Gly Tyr Thr Ala Arg
            245                 250
```